(12) United States Patent
Craighead et al.

(10) Patent No.: US 10,132,798 B2
(45) Date of Patent: Nov. 20, 2018

(54) MULTIPLEXED MICROCOLUMN DEVICES AND PROCESSES FOR SELECTION OF NUCLEIC ACID APTAMERS

(71) Applicant: CORNELL UNIVERSITY, Ithaca, NY (US)

(72) Inventors: Harold G. Craighead, Ithaca, NY (US); David R. Latulippe, Ithaca, NY (US); John T. Lis, Ithaca, NY (US); Abdullah Ozer, Vestal, NY (US); Kylan Szeto, Ithaca, NY (US)

(73) Assignee: CORNELL UNIVERSITY, Ithaca, NY (US)

( * ) Notice: Subject to any disclaimer, the term of this patent is extended or adjusted under 35 U.S.C. 154(b) by 408 days.

(21) Appl. No.: 14/400,229

(22) PCT Filed: May 13, 2013

(86) PCT No.: PCT/US2013/040762
§ 371 (c)(1),
(2) Date: Nov. 10, 2014

(87) PCT Pub. No.: WO2013/170256
PCT Pub. Date: Nov. 14, 2013

(65) Prior Publication Data
US 2015/0204859 A1    Jul. 23, 2015

Related U.S. Application Data

(60) Provisional application No. 61/645,783, filed on May 11, 2012.

(51) Int. Cl.
*C12N 15/10* (2006.01)
*G01N 33/53* (2006.01)
(Continued)

(52) U.S. Cl.
CPC ....... *G01N 33/5308* (2013.01); *C12N 15/115* (2013.01); *G01N 33/48* (2013.01);
(Continued)

(58) Field of Classification Search
None
See application file for complete search history.

(56) References Cited

U.S. PATENT DOCUMENTS 4,510,058 A * 4/1985 Cais ................... B01D 15/1892
                                                210/198.2
6,273,478 B1 * 8/2001 Benett ...................... F15C 5/00
                                                285/338
(Continued)

OTHER PUBLICATIONS

Haiducu et al. (2008) "Deep-UV patterning of commercial grade PMMA for low-cost, large-scale microfluidics" Journal of Micromechanics and Microengineering 18(11):115029.*
(Continued)

*Primary Examiner* — Karen S. Weiler
(74) *Attorney, Agent, or Firm* — FisherBroyles, LLP; Andrew K. Gonsalves, Esq.

(57) ABSTRACT

The present invention relates to a microcolumn device for selecting nucleic acid aptamers for single and multiple target molecules, as well as a method for making the microcolumn device. The present invention also relates to a system for selecting nucleic acid aptamers for single and multiple target molecules. The present invention further relates to methods of using the microcolumn device for selecting nucleic acid aptamers for multiple target molecules. Kits that include one or more microcolumn device and/or system of the present invention are also disclosed.

30 Claims, 16 Drawing Sheets
Specification includes a Sequence Listing.

(51) Int. Cl.
*G01N 33/48* (2006.01)
*C12N 15/115* (2010.01)

(52) U.S. Cl.
CPC ..... *G01N 33/5302* (2013.01); *C12N 2310/16* (2013.01); *C12N 2330/00* (2013.01)

(56) References Cited

U.S. PATENT DOCUMENTS

| | | | |
|---|---|---|---|
| 6,727,104 B2 | 4/2004 | Hage et al. | |
| 2003/0099954 A1 | 5/2003 | Miltenyi et al. | |
| 2004/0245102 A1* | 12/2004 | Gilbert | B01D 63/087 |
| | | | 204/451 |

OTHER PUBLICATIONS

SPI Supplies, product page for Whatman Nuclepore Track-Etch membrane #F0247, https://www.2spi.com/item/f0247-mb/, accessed Nov. 30, 2017.*

International Search Report and Written Opinion issued in International Application No. PCT/US2013/040762, dated Sep. 26, 2013.
International Preliminary Report on Patentability issued in International Application No. PCT/US2013/040762, dated Nov. 20, 2014.
Konishi et al., "High-performance packed glass-lined stainless steel capillary column for microcolumn liquid chromatography," *Analytical Chemistry*, 57(12):2235-2239 (1985).
Ravelet et al., "Recent developments in the HPLC enantiomeric separation using chiral selectors identified by a combinatorial strategy," *Journal of Separation Science*, 29(10):1322-1331 (2006).
Lou et al., "Micromagnetic selection of aptamers in microfluidic channels," *PNAS*, 106(9):2989-2994 (2009).
Latulippe et al., "Multiplexed microcolumn-based process for efficient selection of RNA aptamers," *Analytical Chemistry*, 85(6):3417-3424 (2013).

* cited by examiner

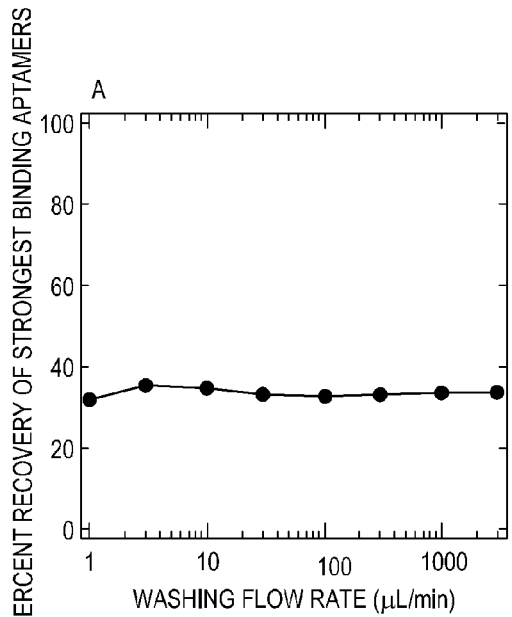
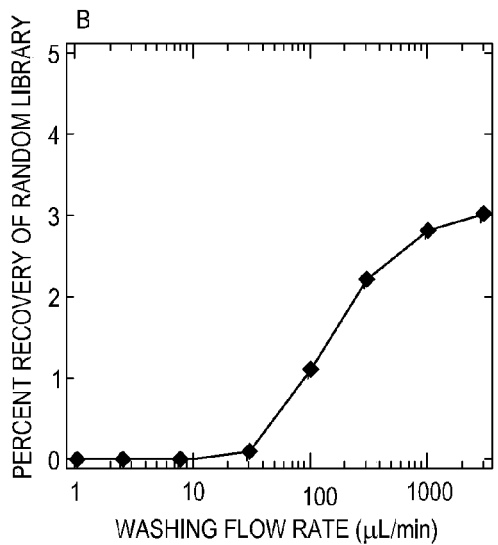
FIG. 20A
FIG. 20B
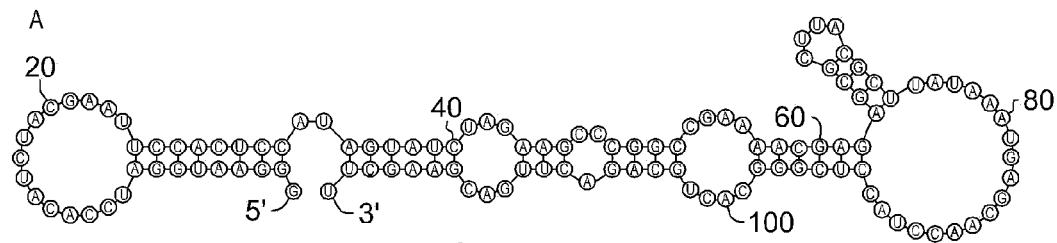
FIG. 21A
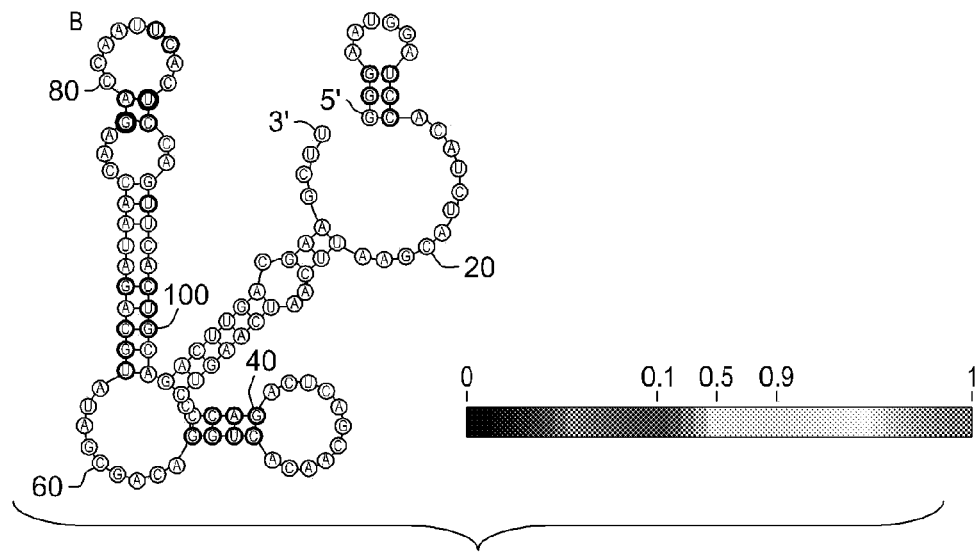
FIG. 21B

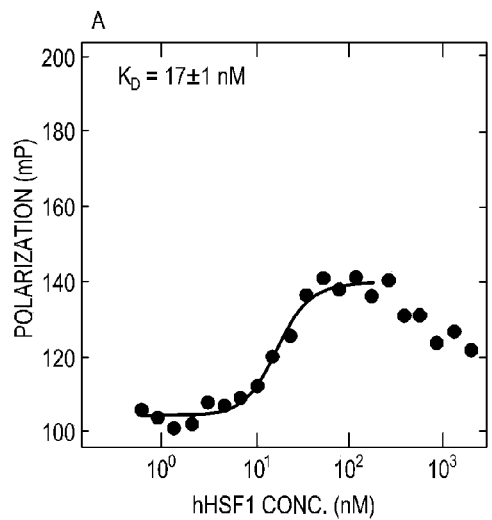
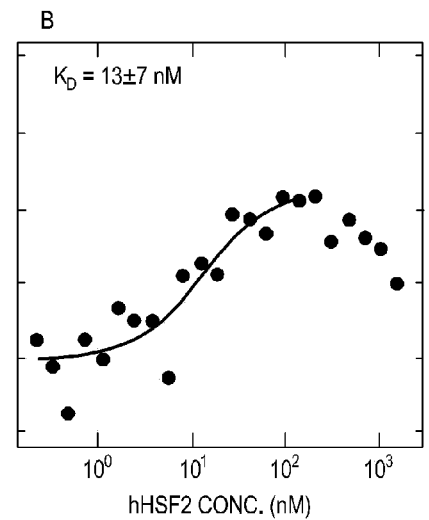
FIG. 23A
FIG. 23B
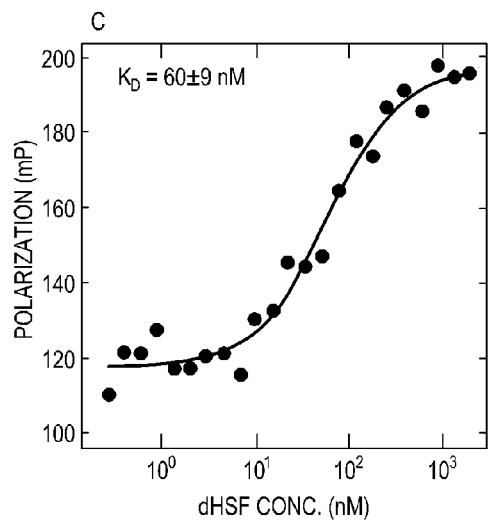
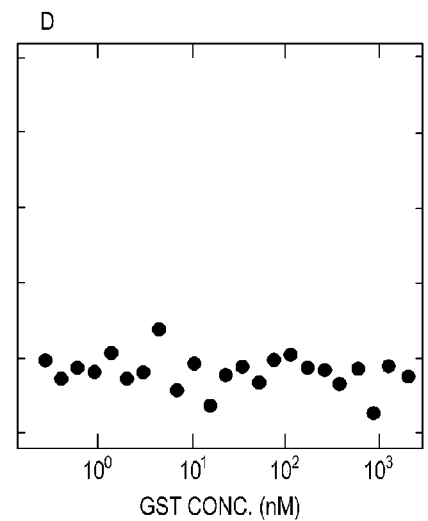
FIG. 23C
FIG. 23D

MULTIPLEXED MICROCOLUMN DEVICES AND PROCESSES FOR SELECTION OF NUCLEIC ACID APTAMERS

CROSS-REFERENCE TO RELATED APPLICATIONS

This application is a U.S. National Phase filing under 35 U.S.C. § 371 of International Application No. PCT/US2013/040762, filed May 13, 2013, and published as WO 2013/170256-A1 on Nov. 14, 2013, which claims benefit of priority from U.S. Provisional Patent Application Ser. No. 61/645,783, filed May 11, 2012. The entire contents of each of the prior applications are incorporated herein by reference in their entirety.

GOVERNMENT RIGHTS STATEMENT

This invention was made with Government support under grant numbers 5R01GM090320-03 and 5R01DA030329-02 awarded by the National Institutes of Health. The United States Government has certain rights in the invention.

FIELD OF THE INVENTION

The present invention relates to a microcolumn device for selecting nucleic acid aptamers for, inter alia, single and multiple target molecules. The present invention also relates to systems and kits that include the microcolumn device of the present invention. Further, the present invention also relates to methods for making and using the microcolumn device of the present invention.

BACKGROUND OF THE INVENTION

Nucleic acid aptamers are short (~100 nt) structured oligonucleotides that have been selected from large sequence-diverse libraries and shown to display high affinity and specificity for a wide range of targets ranging from simple metal ions (Ref. 1) to complex surface proteins on living cells (Ref. 2). This combination of properties has led to growing interest in applications of aptamers in fields including therapeutics, chemical analysis, biotechnology, chemical separations and environmental diagnostics (Ref. 3). Aptamers are identified from large libraries of random nucleic acid sequences via an iterative in vitro process called SELEX (Systematic Evolution of Ligands by EXponential enrichment) (Refs. 4-6). A typical SELEX round includes the following three steps: (i) Binding: incubation of the library with the target; (ii) Partitioning: separation of target-bound library sequences from unbound ones; (iii) Amplification: generation of a new pool of nucleic acids by making multiple copies of the sequences that bound to the target. These steps are then repeated in an iterative fashion to obtain an enriched pool and the target binding aptamers are identified via cloning and sequencing processes.

Different selection strategies have been developed to separate or partition the free and target-bound sequences, a critical step to ensure the successful identification of only the strongest binding aptamers. Affinity chromatography is one such partitioning strategy that uses specific binding onto resin-immobilized targets to purify macromolecular solutes from dilute solutions (Ref. 7). It is a well-documented aptamer selection technique given that it can achieve a level of purification greater than 95% in a single step and that numerous types of resin media are available to bind a wide variety of targets. However, there is limited understanding of the relationship governing the process parameters (target loading, resin volume, etc.) and the selection quality, and thus, many selection rounds (typically 12 to 15) are required to identify aptamers with the desired specificity and affinity for the target. This approach is particularly challenging when working with RNA libraries because it takes approximately two days just to complete the amplification step. Some work has been done to parallelize the use of libraries and the selection process to multiple targets in order to save time and reagents (Refs. 8 and 9).

Affinity chromatography-based selections are typically done in two different modes of operation. In the batch-mode, a small amount of target-immobilized resin (~20 to 200 µL) is incubated with the nucleic acid library or alternatively target-free resin is incubated with a mixed suspension of target and nucleic acid library (Refs. 10-12). Any unbound sequences in the supernatant are removed and the target-bound sequences remaining on the resin are then exposed to other solutions for the subsequent processing steps. For this approach, the entire selection process is quite laborious, because each step must be done manually and repeated several times. This is especially true when multiple targets are considered for selection. The second mode of operation, flow-mode, uses small columns (~0.5 to 3 mL) packed with resin (Refs. 1, 13, and 14). The primary advantage of this approach is that the resin is physically confined within the column, allowing all of the selection steps to be automated using pumps and/or centrifuges and thus completed more efficiently than the batch strategy. This approach was used in one of the landmark papers on aptamers—Ellington and Szostak (Ref. 5) used a 3.5 mL column filled with dye-immobilized resin. However, there are limitations to this approach. The standard columns that have been used previously are not practical for the simultaneous selection of aptamers for multiple targets. These columns require more resin than the batch-mode, as well as more of the immobilized target (e.g., protein), which can be both limiting and expensive. Thus, with the current affinity-chromatography based strategies, there is a noticeable lack of means to rapidly screen for aptamers to multiple targets in a high-throughput and efficient manner.

The present invention is directed to overcoming these and other deficiencies in the art.

SUMMARY OF THE INVENTION

The present invention provides, inter alia, microcolumn devices, systems, methods, and kits for use in various applications, including, without limitation, for the selection of nucleic acid aptamers. The present invention provides advantages over existing aptamer selection technologies. For example, to address the limitations in the art, in one aspect, the present invention provides a process utilizing reconfigurable microcolumn devices of varying capacity for selecting nucleic acid aptamers. In certain embodiments, the microcolumn devices require only microliter volumes of affinity chromatography resin (e.g., ~2 to 50 µL). Further, the microcolumn devices can be easily assembled in various configurations to accommodate multiple targets, and they can be easily integrated with common laboratory equipment. In addition, the microcolumn devices of the present invention are not restricted to RNA and other nucleic acid aptamer selections, but they are also suitable for other affinity chromatography needs where small column volumes are desired.

In one aspect, the present invention relates to a microcolumn device for selecting nucleic acid aptamers for, inter alia, single and multiple target molecules. The microcolumn device includes: (i) a body comprising an inlet end, an outlet end, a recessed portion extending into the body from the outlet end and forming a compartment for housing a frit, and a microfluidic channel disposed between the inlet end and the recessed portion; (ii) a frit (e.g., a porous polymer, a stainless steel frit) disposed in the recessed portion; and (iii) a pair of adapters comprising an inlet adapter bonded to the inlet end of the body and an outlet adapter bonded to the outlet end of the body, wherein each adapter includes a hollow passageway for passing a liquid sample there through, and wherein each adapter includes a connector region for effectuating serial fluid communication of a plurality of microcolumn devices. In one embodiment, the microcolumn device further includes an affinity chromatography resin disposed in the microfluidic channel of the body.

In another aspect, the present invention relates to a system for selecting nucleic acid aptamers for single and multiple target molecules. The system includes a plurality of microcolumn devices in serial fluid communication with one another. Each microcolumn device includes: (i) a body comprising an inlet end, an outlet end, a recessed portion extending into the body from the outlet end and forming a compartment for housing a frit, and a microfluidic channel disposed between the inlet end and the recessed portion; (ii) a frit (e.g., a porous polymer, a stainless steel frit) disposed in the recessed portion; and (iii) a pair of adapters comprising an inlet adapter bonded to the inlet end of the body and an outlet adapter bonded to the outlet end of the body, wherein each adapter includes a hollow passageway for passing a liquid sample there through, and wherein each adapter includes a connector region for effectuating serial fluid communication of the plurality of microcolumn devices. In one embodiment, the system further includes an affinity chromatography resin disposed in the microfluidic channel of the body of each microcolumn device.

In another aspect, the present invention relates to a method of selecting nucleic acid aptamers for multiple target molecules. This method involves: (i) providing a plurality of microcolumn devices according to the present invention that are serially connected with one another, wherein each microcolumn device comprises a different target molecule or no target molecule; (ii) introducing a sample comprising a population of nucleic acid molecules through the serially connected microcolumn devices under conditions effective to allow nucleic acid molecules to bind specifically to the target molecules of each microcolumn device; (iii) rearranging the serially connected microcolumn devices into either a standalone or parallel configuration; (iv) removing from the rearranged microcolumn devices substantially all nucleic acid molecules that do not bind specifically to the target molecules of each microcolumn device; and (v) recovering from each microcolumn device nucleic acid molecules that bind specifically to the respective target molecules of each microcolumn device, the recovered nucleic acid molecules being aptamers that have been selected for their binding to the respective target molecules. In one embodiment, the nucleic acid aptamers comprise RNA aptamers, and the method further involves performing reverse transcription amplification of the selected aptamer population. In a particular embodiment, the method further involves purifying and sequencing the amplified apatmer population.

In another aspect, the present invention relates to a method of making a microcolumn device for selecting nucleic acid aptamers for single and multiple target molecules. This method involves: (i) providing a body comprising an inlet end, an outlet end, a recessed portion extending into the body from the outlet end and forming a compart- ment for housing a frit, and a microfluidic channel disposed between the inlet end and the recessed portion; (ii) disposing a frit (e.g., a porous polymer, a stainless steel frit) in the recessed portion of the body; and (iii) attaching a pair of adapters to the body, wherein an inlet adapter is bonded to the inlet end of the body and an outlet adapter is bonded to the outlet end of the body, wherein each adapter includes a hollow passageway for passing a liquid sample there through, and wherein each adapter includes a connector region for effectuating serial fluid communication of multiple microcolumn devices. In one embodiment, this method further involves disposing an affinity chromatography resin in the microfluidic channel of the body.

In another aspect, the present invention relates to a kit comprising one or more microcolumn devices according to the present invention.

In another aspect, the present invention relates to a kit comprising one or more systems according to the present invention.

As described herein, aspects of the present invention relate to microcolumn devices (see, e.g., FIG. 1) that can be used in serial connection and then reconfigured in stand-alone and/or parallel configurations for the efficient selection of aptamers to multiple targets. In various embodiments, the microcolumn devices have been designed to have, but are not limited to, a number of features, as follows: (i) they require very little amounts of affinity chromatography resin; (ii) they can be fabricated from inexpensive, readily-available plastic materials that can be easily machined and processed (e.g., all of the components can be autoclavable and thus can be re-used in multiple selection rounds); (iii) they can be easily assembled into a variety of configurations to accommodate multiple targets or non-conventional selection strategies; (iv) they can be used with a wide variety of affinity chromatography media (e.g., immobilized metal, glutathione, protein A/G, avidin/biotin) in both the more common bead-based and monolithic formats; (v) they are readily compatible with standard 96-well plates for subsequent sample processing steps; and (vi) they are optically transparent to allow for monitoring and characterization of all the selection and amplification steps.

During operation of the microcolumn devices of the present invention, with respect to the variety of configurations of the microcolumn devices, at any point during a selection round, they can be re-assembled into other configurations. This feature allows for specific elution of the bound nucleic acids only from the desired targets. As an illustrative example of one embodiment, FIG. 11 shows the entire selection and amplification steps for one strategy where the initial nucleic acid library is loaded onto three microcolumn devices connected in series. The devices are disconnected and reconfigured into a parallel orientation for the subsequent washing and elution steps. FIGS. 2A-2B show two sets of microcolumn devices connected to a syringe pump in the two different configurations described above.

As depicted in FIGS. 2A-2B, they can be easily connected to common laboratory equipment such as syringe pumps. They can also be integrated with high-performance liquid chromatography systems to allow for real-time monitoring and subsequent optimization of the selection process.

Given all the features described above, the microcolumn devices of the present invention can be readily used to systematically explore the very large chromatographic design space that is used for selecting aptamers. Thus, the microcolumn device based approach of the present invention facilitates the development of high throughput and efficient aptamer selection procedures.

These and other objects, features, and advantages of this invention will become apparent from the following detailed description of the various aspects of the invention taken in conjunction with the accompanying drawings.

BRIEF DESCRIPTION OF THE DRAWINGS

For the purpose of illustrating aspects of the present invention, there are depicted in the drawings certain embodiments of the invention. However, the invention is not limited to the precise arrangements and instrumentalities of the embodiments depicted in the drawings. Further, as provided, like reference numerals contained in the drawings are meant to identify similar or identical elements.

FIG. 2A shows a system 100 of the present invention where the microcolumn devices are arranged in serial fluidic communication with one another. FIG. 2B shows a system 200 of the present invention where the microcolumn devices are arranged in parallel with one another.

FIGS. 20A-20B. Simulation results for the effect of washing flow rate on percent recovery of a strong binding aptamer ($K_D$=5 nM) (FIG. 20A) and random library molecules (FIG. 20B). The other simulations parameters were total resin volume=10 μL, concentration of immobilized target protein=22 μM, and loading flow rate=100 μL/min.

FIGS. 21A-21B. Mfold predicted secondary structures of hHSF1-R5-1 (FIG. 21A) and hHSF2-R5-2 (FIG. 21B); the full sequences for these putative RNA aptamers were 5'-<u>GGGAAUGGAUCCACAUCUACGAAUUCCACUCC</u> AUAGUAUCUA GAAGCCCUGCCGAAAACGA- GAGCGCUUACGCUUAUAAAUGAUCAACCUACCUC <u>GUUCACUGCAGACUUGACGAAGCUU-3'</u> (SEQ ID NO:21) and 5'- <u>GGGAAUGGAUCCACAUCUACGAAUUCAAUCAAG</u> UCCCCAGACUCAGCAACACUGGACAGCGA UAUGCAGAUAACCAAGACCAAUUCACUCCAG <u>UUCACUGCAGACUUGACGAAGCUU-3'</u> (SEQ ID NO:22), respectively. The two constant regions corresponding to the library design are denoted by underlines. The structures are annotated using p-num with the color representing the probability according to the color legend.

FIGS. 23A-23D. Fluorescence polarization (FP) assay results for binding of hHSF2-R5-2 aptamer to GST-hHSF1 (FIG. 22A), GST-hHSF2 (FIG. 22B), hexahistidine-dHSF (FIG. 22C), and GST-tag (FIG. 22D). The solid line in each panel (except FIG. 22D) is the best-fit of the Hill equation to the experimental data with the given $K_D$ value.

DETAILED DESCRIPTION OF THE INVENTION

Figure 1:
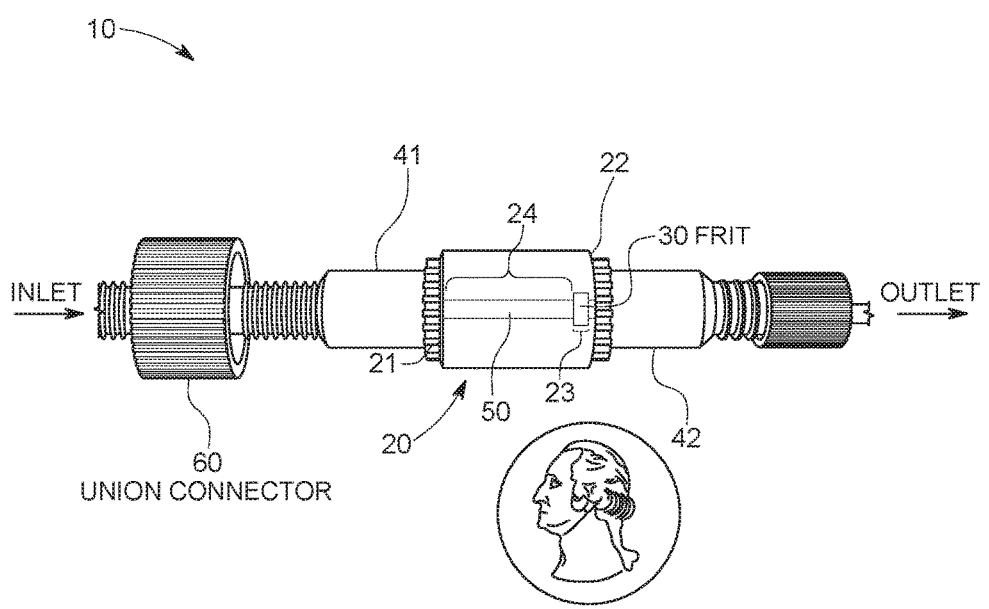
FIG. 1 shows one embodiment of a microcolumn device of the present invention. In the embodiment shown, the microcolumn device (total volume=10 μL) is filled with Ni-NTA resin pre-loaded with green fluorescent protein (GFP-immobilized chromatography resin). The porous polymer frit retains the resin within the microfluidic channel 24 of microcolumn device 10. The male-male union connector is used to connect multiple devices or to connect the device(s) to other laboratory equipment.

The present invention generally relates to, inter alia, devices, systems, and methods for selecting nucleic acid aptamers for various targets (e.g., single and multiple target molecules). In addition, the devices, systems, and methods of the present invention can also be used to select for multiple distinct aptamers to a single target. This aspect involves the same general scheme as that used to select aptamers for multiple targets, but is designed to generate multiple distinct binders, so that the target can be multiply labeled, or used in sandwich assays, or in aptamer-based ELISA, or to specifically manipulate or modulate binding at a precise location.

In one aspect, the present invention relates to a microcolumn device for selecting nucleic acid aptamers for single and multiple target molecules. The microcolumn device includes: (i) a body comprising an inlet end, an outlet end, a recessed portion extending into the body from the outlet end and forming a compartment for housing a frit, and a microfluidic channel disposed between the inlet end and the recessed portion; (ii) a frit disposed in the recessed portion; and (iii) a pair of adapters comprising an inlet adapter bonded to the inlet end of the body and an outlet adapter bonded to the outlet end of the body, wherein each adapter includes a hollow passageway for passing a liquid sample there through, and wherein each adapter includes a connector region for effectuating serial fluid communication of a plurality of microcolumn devices.

In one embodiment, the microcolumn device of the present invention is serially connected to at least one other microcolumn device of the present invention during operation. That same microcolumn device may also be subsequently detached from the serial connection and reattached in parallel with another microcolumn device or kept detached from another micocolumn device during operation.

The body of the microcolumn device of the present invention can made of any biocompatible material that is suitable for forming a microfluidic channel in which an affinity chromatography resin can be maintained and through which a liquid sample containing nucleic acids (e.g., apatmers) can be passed for affinity chromatographic applications. In one embodiment, the body of the microcolumn device is made from a biocompatible plastic polymer. Suitable examples of biocompatible plastic polymers for use in make the body can include, without limitation, poly(ethylene terephthalate glycol) (PETg), polyvinyl chloride (PVC), poly(methyl methacrylate) (PMMA), and the like. The biocompatible material, when formed into the body, can be transparent, semi-transparent, or non-transparent.

As described herein, the body includes an inlet end, an outlet end, a recessed portion extending into the body from the outlet end and forming a compartment for housing a frit, and a microfluidic channel disposed between the inlet end and the recessed portion. Therefore, suitable biocompatible materials making up the body of the microcolumn device of the present invention include any such material effective to be formed as previously described.

As described herein, the microcolumn device includes a frit that is disposed in the recessed portion of the body of the microcolumn device. Therefore, in various embodiments, the frit is of a form and size sufficient to be disposed in the recessed portion of the body. Suitable frits for use in the present invention can include any frit that can be used for maintaining an affinity chromatography resin in the microfluidic channel of the body of the microcolumn device of the present invention, while at the same time allowing a liquid sample of nucleic acids (e.g., apatamers) to pass through the frit and then out of the outled end of the body and ultimately out of the outlet adapter. For example, a suitable frit can be made of a porous polymer (e.g., polyethylene), stainless steel, or any other material that is biocompatible and that can function as a frit to maintain the affinity chromatography resin in the microfluidic channel.

As described herein, the microcolumn device of the present invention includes a pair of adapters comprising an inlet adapter and an outlet adapter. The inlet adapter is bonded to the inlet end of the body and and the outlet adapter is bonded to the outlet end of the body. Each of the adapters includes a hollow passageway for passing a liquid sample there through. Further, each adapter includes a connector region for effectuating serial fluid communication of a plurality of microcolumn devices.

Provided below is one exemplary embodiment of how the microcolumn device of the present invention can be fabricated. For example, the microcolumn device can be assembled using both custom fabricated and commercially available parts. In one embodiment, the body of the microfluidic column comprises a transparent biocompatible plastic rod fitted with a porous frit that retains a resin in the device (see FIG. 1). By varying both the length and internal diameter of the microfluidic channel, one is able to fabricate microcolumn devices having microfluidic changes having a range of volume capacities. For example, the volume capacity of the microfluidic channel can range from between about 0.5 and about 250 µL, from between about 1 and about 200 µL, from between about 2 µL and about 150 µL, from between about 5 µL and about 100 µL, and from about 10 µL and about 50 µL. In a particular embodiment, the volume capacity of the microfluidic channel can range from about 0.5 µL and about 100 µL, and more particularly from about 2 µL and about 50 µL.

NanoPorts (IDEX Health & Science) that accommodate standard tubing connectors can bonded to either end of the body of the microcolumn device. Overall, this design has a number of advantageous features: simple union connectors can be used to arrange multiple microcolumn devices into various configurations, the 'dead volume' between the microcolumn devices is minimized and is generally less than 1 µL, and the microcolumn devices can be connected to common laboratory equipment to automate the selection steps (as discussed herein). For example, to perform the multiple target aptamer selection, a workflow process can be followed wherein a set of microcolumns, each pre-filled with a different target-immobilized resin, are arranged into a serial configuration (see FIG. 11). A pump system can be arranged in order to accommodate a plurality of parallelized assemblies of microcolumn devices (e.g., up to ten parallelized assemblies of microcolumn devices, but the general approach can easily be scaled up for a larger number of parallel processes).

Figure 11:
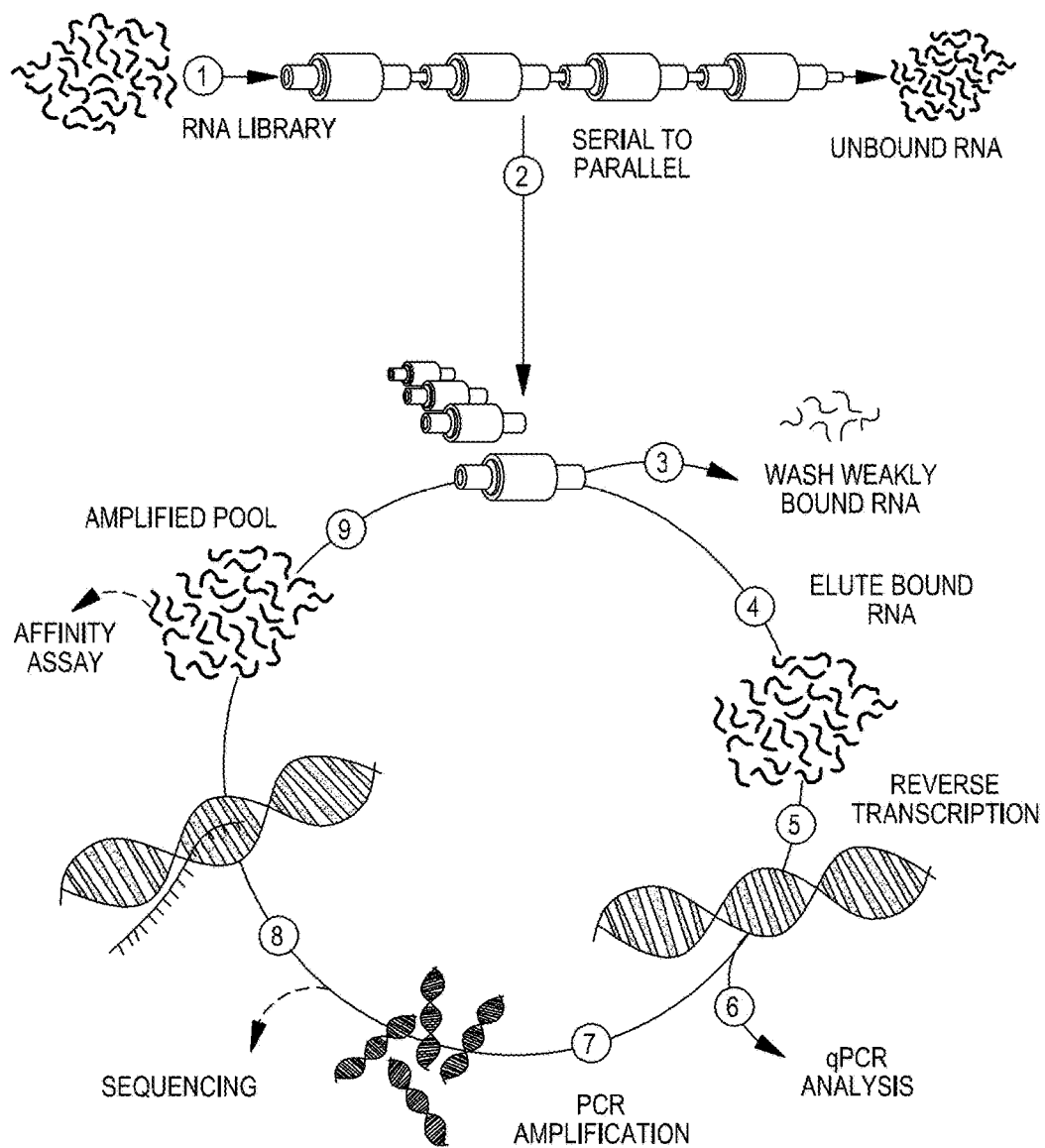
FIG. 11 is a schematic representation of the use of the microcolumn devices of the present invention in microcolumn based aptamer selection. Briefly, in the embodiment shown, the RNA library is loaded onto multiple microcolumns arranged in a serial configuration; the different colors indicate different aptamer targets. The devices are then manually rearranged into the parallel configuration. All of the subsequent processing steps are done for all the micro-columns but are only shown for the one microcolumn. Weakly bound RNA are washed away and the remaining RNA-target complexes are eluted out of the column. The RNA molecules are reverse transcribed into DNA and a small fraction is used in the qPCR analysis to determine the amount of input RNA that was retained on the microcolumn device after the washing step. The residual amount of DNA is amplified and then transcribed back into RNA to make a new pool for the next selection round.

During operation of the microcolumn devices, a single aliquot of the starting random library can be flowed through these devices allowing the target binding aptamers to be captured on the resin within each individual microcolumn device. The library molecules that do not bind to any target are discarded and then the individual microcolumns are disconnected and reorganized into a parallel configuration (FIG. 11). This arrangement allows for specific elutions from each target and thus separate processing of only the bound sequences to create target-specific amplified pools for the next selection round. In a particular embodiment, following the RNA reverse transcription of the RNA aptamer into cDNA, one can use quantitative PCR (qPCR) to determine the amount of nucleic acid recovered from each device. This information can be used to determine the optimal number of PCR cycles and thus minimize the chance of amplification artifacts. Although FIG. 1B shows the microcolumns arranged exclusively in a parallel configuration after the first selection round, it is also possible to use a serial configuration in later rounds. This arrangement would allow for negative or counter selections to be done simultaneously with the selection step to enhance specificity for the target.

In choosing the size of the microcolumns, various objectives can be considered. For example, one objective can be to size the microcolumns small enough so that they require only relatively small amounts of material for each selection round, but to have internal dimensions that are sufficiently large enough so that they can be easily filled with a variety of different resins. Further, binding kinetic simulations can be used to determine microcolumn size.

In one embodiment, the microcolumn device further includes an affinity chromatography resin disposed in the microfluidic channel of the body. As used herein, any affinity chromatography resin for selecting for aptamers can be used in the microcolumn device of the present invention. In a particular embodiment, the affinity chromatography resin can include an immobilized target molecule. In another particular embodiment, the immobilized target can be labeled. The immobilized target molecule can be any molecule that binds to a nucleic acid aptamer. For example, the immobilized target molecule can be, without limitation, a protein or polypeptide, a carbohydrate, a lipid, a small molecule, a pharmaceutical agent, an organic non-pharmaceutical agent, a macromolecular complex, a virus particle, or a cell (e.g., a yeast cell). In particular embodiments, the immobilized target molecule is provided from a mixture of lysed cells, a mixture of purified, partially purified, or non-purified protein.

The microcolumn device and related systems and methods of the present invention can been used for various targets. For example, certain of the proteins analyzed as targets by the microcolumn device of the present invention and its related systems and methods include His-tagged proteins (6×Histadine), GST-tagged proteins (glutathione S-transferase), MBP-tagged proteins (Maltose Binding Protein), and the like.

His-tagged proteins (6×Histadine) were immobilized by simple incubation with Ni-NTA resin. Washes can be done using 10-20 mM Imidazole in buffers. Elutions can be done with high concentrations of imidazole or EDTA which recover both the protein and bound aptamers.

GST-tagged proteins (glutathione S-transferase) were immobilized by simple incubation with glutathione resin. Washes can be done using high-salt buffers. Elutions can be done with high concentration of glutathione which recover both the protein and bound aptamers.

MBP-tagged proteins (Maltose Binding Protein) were immobilized by simple incubation with Amylose resin. Washes can be done using high-salt buffers. Elutions can be done with high concentration of Maltose which recover both the protein and bound aptamers.

As one example, targets can be biotinylated using a cleavable tag containing a disulfide bond. These can be immobilized onto Streptavidin resin. Washes can be done with high-salt buffer. Elutions can be done using DTT or BME to cleave the tag at the disulfide bond. Alternatively, biotinylated targets can be immobilized onto SoftLink Soft Release Avidin Resin, and Eluted with high concentrations of Streptavidin.

Examples of peptides that can be analyzed as targets by the microcolumn device of the present invention and its related systems and methods include, without limitation, His-tagged peptides that were immobilized, washed, and eluted similar to above; cysteine terminated peptides, which are covalently reacted to resins via sulfhydryl; biotinylated peptides, which can be immobilized on streptabidin resin; and peptides that can be immobilized to various resins via the N-terminal amino group or the C-terminal carboxyl group.

Examples of cells or cell portions that can be analyzed as targets by the microcolumn device of the present invention and its related systems and methods can include, without limitation, cell surface proteins (e.g., on yeast) and mammalian cells, although any cells are contemplated as targets of the present invention. With respect to cell surface proteins (e.g., on yeast), such cell surface proteins (on yeast) were biotinylated, and then incubated with Streptavidin Resin. Washes can be done with high-salt buffers. Elutions can be done using DTT or BME to cleave the protein which was expressed on the cell surface with a Disulfide bond. The biotinylated proteins and the target protein are different to prevent steric hinderance, limit recovery of the protein-aptamer complex, leaving the cell behind. This can be done in general with any cells, including mammalian cells.

Examples of small molecules that can be analyzed as targets by the microcolumn device of the present invention and its related systems and methods can include, without limitation, small molecules dyes. Small Dye molecules are synthesized with reactive groups for immobilization. Washes can be done with high-salt buffers. Elutions can be done using high concentrations of free dye to compete off bound aptamers.

As provided herein, other aspects of the present invention include and/or relate to the use of the microcolumn device of the present invention. Therefore, any embodiments, attributes, and/or other aspects of the microcolumn device of the present invention that are not reiterated with respect any of the systems, methods, or kits of the present invention are hereby incorporated by reference with respect to those systems, methods, and kits.

In another aspect, the present invention relates to a system for selecting nucleic acid aptamers for single and multiple target molecules. The system includes a plurality of microcolumn devices in serial fluid communication with one another. Each microcolumn device includes: (i) a body comprising an inlet end, an outlet end, a recessed portion extending into the body from the outlet end and forming a compartment for housing a frit, and a microfluidic channel disposed between the inlet end and the recessed portion; (ii) a frit disposed in the recessed portion; and (iii) a pair of adapters comprising an inlet adapter bonded to the inlet end of the body and an outlet adapter bonded to the outlet end of the body, wherein each adapter includes a hollow passageway for passing a liquid sample therethrough, and wherein each adapter includes a connector region for effectuating serial fluid communication of the plurality of microcolumn devices.

In one embodiment, the system further includes an affinity chromatography resin disposed in the microfluidic channel of the body of each microcolumn device. The affinity chromatography resins contained in each microcolumn device can be the same, different, or a combination thereof. In a particular embodiment of this system, the affinity chromatography resin comprises an immobilized target molecule. The immobilized target molecule being can be labeled or unlabeled. In one embodiment, the immobilized target molecules contained in each microcolumn device can be the same, different, or a combination thereof. In another embodiment of the system, union connectors can be used to effectuate the serial fluid communication of the plurality of microfluidic devices.

In another aspect, the present invention relates to a method of selecting nucleic acid aptamers for multiple target molecules. This method involves: (i) providing a plurality of microcolumn devices according to the present invention that are serially connected with one another, wherein each microcolumn device comprises a different target molecule or no target molecule; (ii) introducing a sample comprising a population of nucleic acid molecules through the serially connected microcolumn devices under conditions effective to allow nucleic acid molecules to bind specifically to the target molecules of each microcolumn device; (iii) rearranging the serially connected microcolumn devices into either a standalone or parallel configuration; (iv) removing from the rearranged microcolumn devices substantially all nucleic acid molecules that do not bind specifically to the target molecules of each microcolumn device; and (v) recovering from each microcolumn device nucleic acid molecules that bind specifically to the respective target molecules of each microcolumn device, the recovered nucleic acid molecules being aptamers that have been selected for their binding to the respective target molecules.

In one embodiment, the nucleic acid aptamers comprise RNA aptamers, and the method further involves performing reverse transcription amplification of the selected aptamer population. In a particular embodiment, the method further involves purifying and sequencing the amplified apatmer population.

In one embodiment of this method, the recovering step comprises: (i) washing unbound and weakly bound nucleic acid molecules from each microcolumn device; and (ii) eluting the nucleic acid molecules that specifically bind to the target molecules of each microcolumn device, wherein the eluted nucleic acid molecules are aptamers that bind to the target molecules.

In a particular embodiment of this method, the recovering, the performing reverse transcription amplification, the purifying, and/or the sequencing are performed in one or more separate fluidic devices coupled in fluidic communication with the microcolumn devices of the present invention. In a further embodiment of this method, the introducing, removing, and recovering is automated.

In another aspect, the present invention relates to a method of making a microcolumn device for selecting nucleic acid aptamers for single and multiple target molecules. This method involves: (i) providing a body comprising an inlet end, an outlet end, a recessed portion extending into the body from the outlet end and forming a compartment for housing a frit, and a microfluidic channel disposed between the inlet end and the recessed portion; (ii) disposing a frit (e.g., a porous polymer or stainless steel frit) in the recessed portion of the body; and (iii) attaching a pair of adapters to the body, wherein an inlet adapter is bonded to the inlet end of the body and an outlet adapter is bonded to the outlet end of the body, wherein each adapter includes a hollow passageway for passing a liquid sample there through, and wherein each adapter includes a connector region for effectuating serial fluid communication of multiple microcolumn devices. In one embodiment, this method further involves disposing an affinity chromatography resin in the microfluidic channel of the body. In a particular embodiment, the affinity chromatography resin can include an immobilized target molecule. The immobilized target can be labeled or unlabeled.

In another aspect, the present invention relates to a kit comprising one or more microcolumn devices according to the present invention. In another aspect, the present invention relates to a kit comprising one or more systems according to the present invention. These kits can further include one or more of the following: one or more affinity chromatography resins, one or more labels for tagging a target molecule of interest, a random pool of nucleic acid molecules, wash buffer, binding buffer, blocking buffer, reagents for carrying out reverse transcription, polymerase chain reaction, and/or transcription, and directions for carrying out selection of aptamers to multiple target molecules using a plurality of the microcolumn devices connected in series and subsequently arranged in a standalone or parallel configuration.

The microcolumn device of the present invention and its related systems and methods can be used with various types of libraries, including, without limitation, RNA libraries, DNA libraries, genomic RNA (e.g., GRO-Seq Library), modified nucleic acid libraries (e.g., amplifiable libraries), and the like. For example, with respect to the RNA library, this library can be handled according to knowledge contained in the relevant art. Reverse Transcription, PCR amplification, and Transcription reactions can be employed. For DNA libraries, one example can be to use 5'phosphoralated reverse primers in PCR steps, and Lambda exonuclease to digest complementary DNA strand after amplification. No reverse transcription or transcriptions are needed.

With regard to washes used in the methods of the present invention, in general, washes can include mild detergents. Washes can include mild heat to dissociate weakly bound species. Washes can include high concentrations of negative targets such as the tagging complexes (e.g., His, GST, MBP, etc.) or similar targets in order to ensure high specificity of aptamers to the desired target.

With regard to elutions used in the methods of the present invention, in general, elutions can also be done using EDTA which tends to disrupt the structure of aptamers, causing them to fall apart. Elutions can also be done using heat to denature the protein and/or aptamer causing the bound complex to all apart. Elutions can also be done using high concentrations of the target itself. This causes aptamers bound to immobilized targets to compete for binding with the free target in solution.

As provided herein, multiple microcolumn devices of the present invention can be used for a variety of applications, including, without limitation, multiplexed applications (e.g., multiple independent selections), negative selections, multivalent aptamer isolation, and the like.

With respect to multiplexed/multiple independent selections (i.e., order does not matter), the microcolumn device of the present invention and its related systems and methods can be used on dissimilar targets simultaneously by connecting multiple columns together. These can be washed and eluted in parallel. This partitions the RNA starting pool into N-subpools making more efficient use of that reagent.

With respect to negative selections, one or more column can be added in serial with a target protein in order to do target dependent negative selections (i.e., order matters). This could include the tagging complexes (e.g., His, GST, MBP, etc.) or similar targets in order to ensure aptamers with high specificity to the desired target.

With respect to multivalent aptamer isolation, the microcolumn device of the present invention and its related systems and methods can be used to make simple selections to a target that can be done using a full length protein complex of multiple domains. The last selection steps can be done with the individual domains isolated in different columns. By connecting these in serial, aptamers from the enriched pool can be partitioned according to the domain that they show binding to (order independent). This eliminates redundant work processing and selecting aptamers to each domain separately in parallel. In addition, it ensures that aptamers associate with the full length protein complex while also specifically with the domain.

To further illustrate various aspects of the present invention, provided below is more disclosure in view of various figures provided herein.

As shown in FIG. 1, in one aspect, the present invention relates to a microcolumn device 10 for selecting nucleic acid aptamers for, inter alia, single and multiple target molecules. Microcolumn device 10 includes body 20, frit 30, and a pair of adapters (i.e., inlet adapter 41 and outlet adapter 42). Body 20 includes the following: inlet end 21; outlet end 22; recessed portion 23 extending into body 20 from outlet end 22 and forming a compartment for housing frit 30; and microfluidic channel 24 disposed between inlet end 21 and the recessed portion. Frit 30 (e.g., a porous polymer, a stainless steel frit) is disposed in the recessed portion. The pair of adapters comprises inlet adapter 41 bonded to inlet end 21 of body 20 and outlet adapter 42 bonded to outlet end 22 of body 20, wherein each adapter includes a hollow passageway for passing a liquid sample there through, and wherein each adapter includes a connector region for effectuating serial fluid communication of a plurality of microcolumn devices. As shown in FIG. 1, in this embodiment, microcolumn device 10 further includes affinity chromatography resin 50 disposed in microfluidic channel 24 of body 20. Microcolumn device 10 includes inlet adapter 41 that is attached to union connector 60, which facilitates the serial fluid connection of microcolumn device 10 with other microcolumn devices or with other laboratory equipment used in various applications for aptamer selection, elution, etc.

Figure 2A:
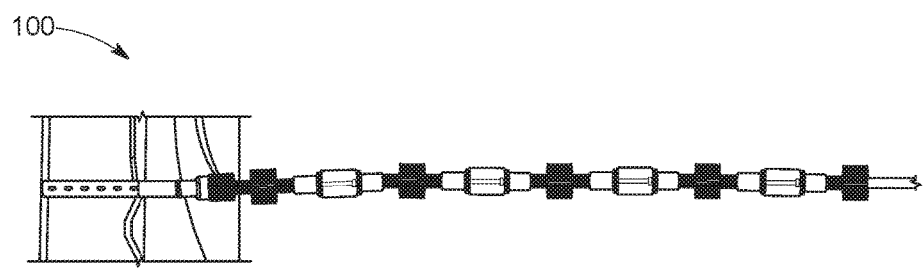
FIGS. 2A-2B show embodiments of a systems of the present invention.
Figure 2B:
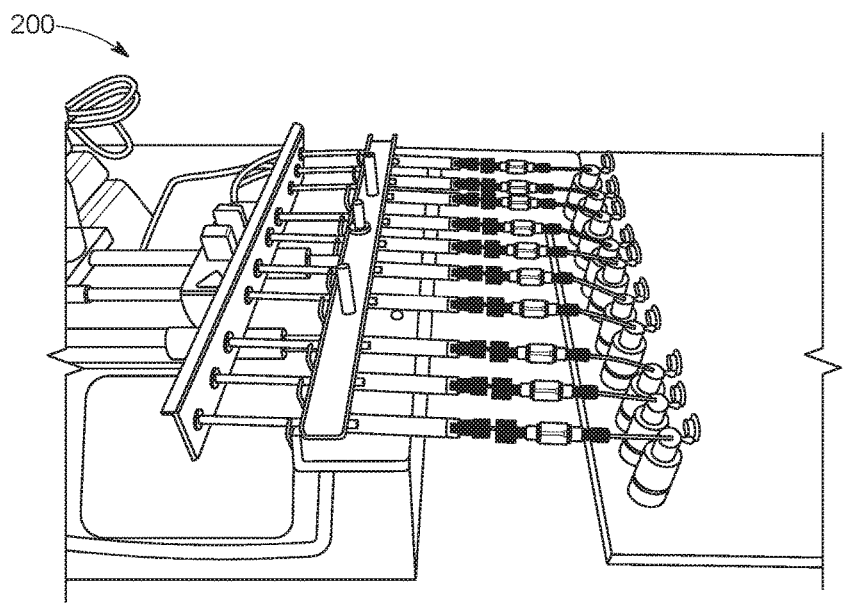

As shown in FIGS. 2A-2B, in certain embodiments, a plurality of microcolumn devices of the present invention can be combined in a system 100 or system 200 of the present invention for selecting nucleic acid aptamers. FIG. 2A shows system 100 of the present invention where the microcolumn devices are arranged in serial fluidic communication with one another, while FIG. 2B shows system 200 of the present invention where the microcolumn devices are arranged in parallel with one another. More specifically, FIG. 2A shows four microcolumn devices arranged in a serial configuration (for loading the RNA library) on a laboratory syringe pump. The syringe is on the far left and thus the direction of flow is from left to right. More specifically, FIG. 2B shows ten microcolumn devices arranged in a parallel configuration (for eluting the RNA-protein complexes) on the same syringe pump shown in FIG. 2A. The direction of flow is again from left to right. The green tubing at the outlet of each device is used to direct the contents into the sample tubes for the subsequent processing steps that are depicted in detail in FIG. 11.

Figure 3:
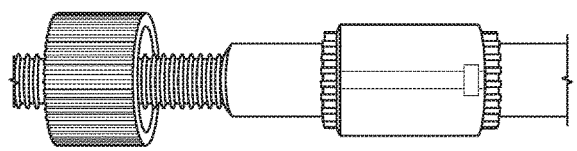
FIG. 3 is a photograph of one embodiment of a microcolumn device of the present invention, along with a union connector attached to the inlet adapter of the microcolumn device.

As shown in FIG. 3, in one embodiment, the microcolumn device of the present invention can be connected to a union connector, which is attached to the inlet adapter of the microcolumn device.

Figure 4:
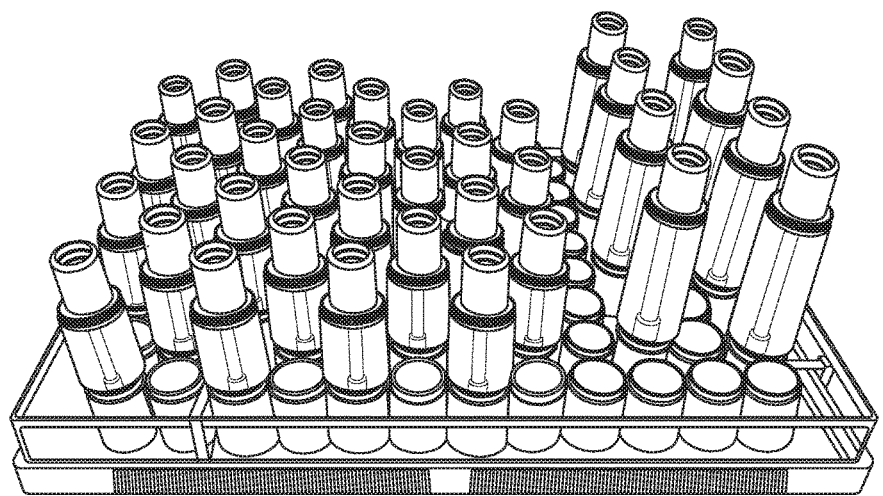
FIG. 4 is a photograph showing a plurality of various embodiments of the microcolumn device of the present invention. As shown, the microcolumn device of the present invention can be configured with varying sizes of bodies.

As shown in FIG. 4, the microcolumn device of the present invention can be provided in a plurality of different body sizes and microfluidic channel volume capacities, depending on the application. FIG. 4 also illustrations how the microcolumn devices may be stored or even used along with other standard laboratory equipment (e.g., well plates).

Figure 5:
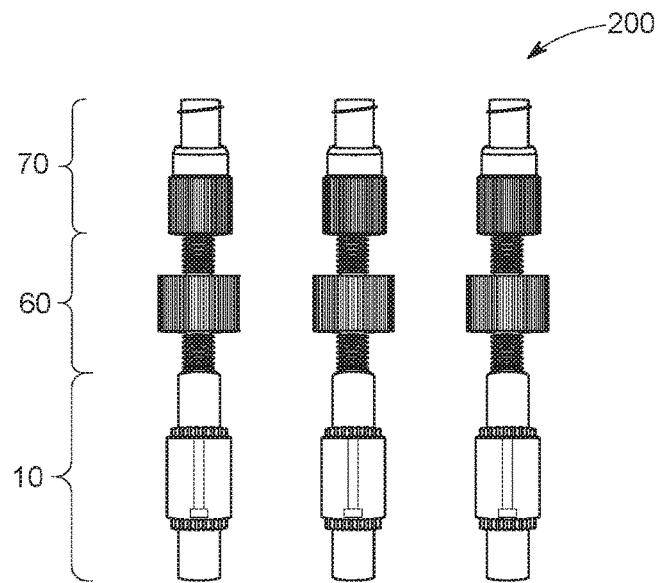
FIG. 5 is a photograph showing one embodiment of system 200 of the present invention for selecting nucleic acid aptamers, where system 200 includes multiple microcolumn devices arranged in a standalone or parallel configuration, in that they are not connected to one another.

As shown in FIG. 5, in one embodiment, the present invention provides system 200 selecting nucleic acid aptamers, where system 200 includes multiple microcolumn devices 10 arranged in a standalone or parallel configuration, in that they are not connected to one another. As shown in FIG. 5, in one embodiment, system 200 includes three microcolumn devices 10, each of which is connected to conduit connectors 70 by union connectors 60. Conduit connectors 70 can be used to attach the system to other laboratory equipment used in aptamer selection, elution, etc. Further, conduit connectors 70 can be used as an outlet for the sample after being passed through microcolumn device 10.

Figure 6:
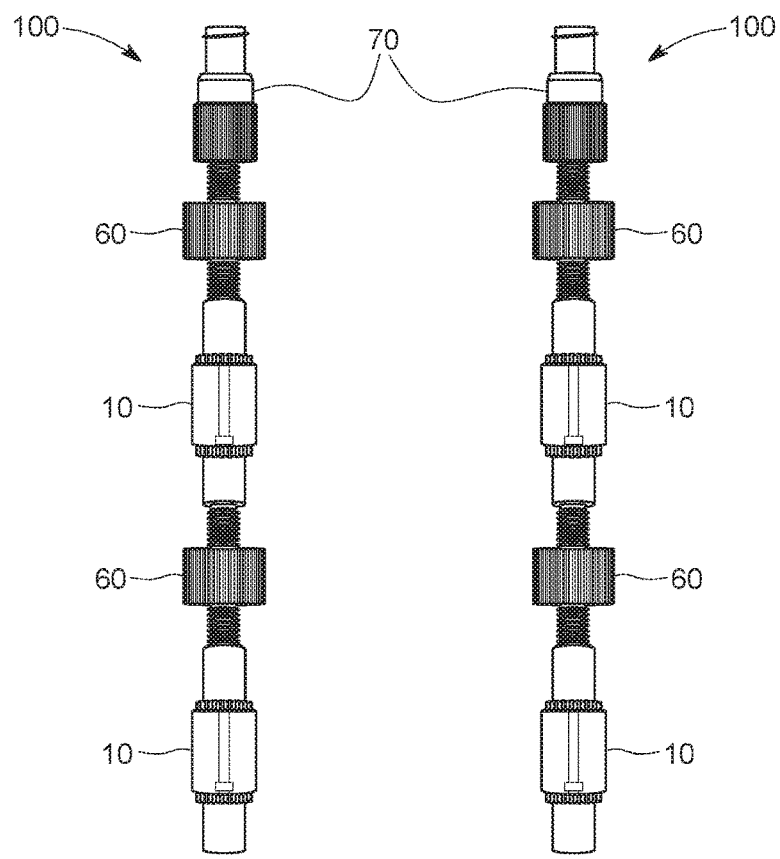
FIG. 6 is a photograph showing embodiments of system 100 of the present invention for selecting nucleic acid aptamers, wherein system 100 includes multiple microcolumn devices arranged in serial fluidic connection with one another.
Figure 7:
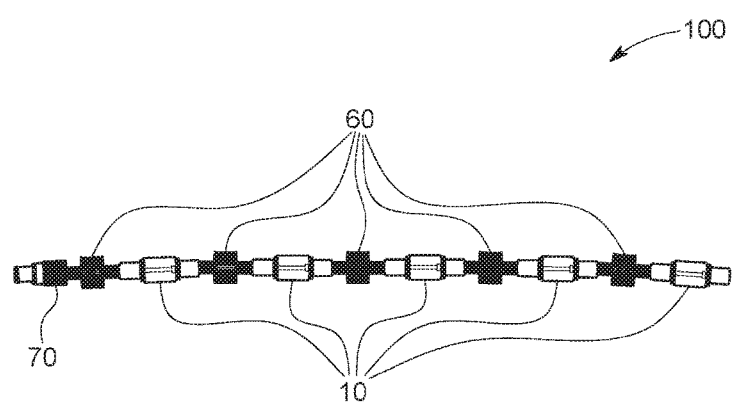
FIG. 7 is a photograph showing one embodiment of system 100 of the present invention for selecting nucleic acid aptamers, wherein system 100 includes multiple microcolumn devices arranged in serial fluidic connection with one another.
Figure 8:
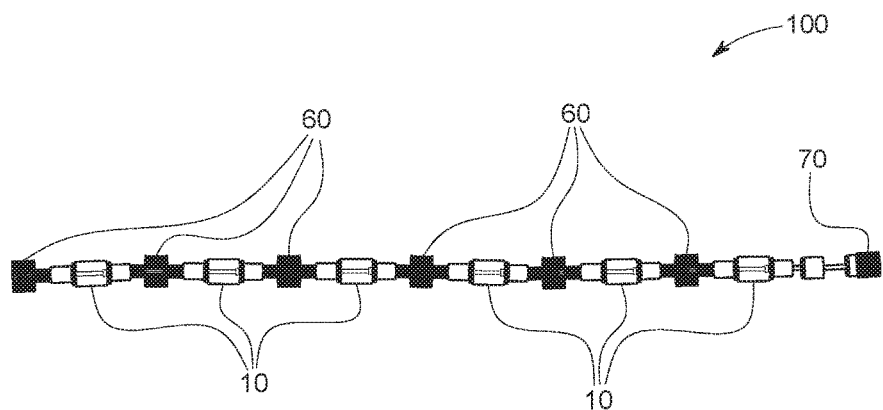
FIG. 8 is a photograph showing one embodiment of system 100 of the present invention for selecting nucleic acid aptamers, wherein system 100 includes multiple microcolumn devices arranged in serial fluidic connection with one another.

As shown in FIGS. 6-8, in various embodiments, the present invention provides system 100 for selecting nucleic acid aptamers, wherein system 100 includes multiple microcolumn devices 10 arranged in serial fluidic connection with one another. As shown in FIG. 6, in one embodiment, system 100 includes two microcolumn devices 10 connected to one another by a union connector 60, with one of the microcolumn devices 10 further being connected to a terminal conduit connector 70 by another union connector 60. In operation, the two systems 100 can be used in conjunction with one another (e.g., using the same pump system to move a sample through both systems 100 at the same time), or they can be used independently of one another. As shown in FIG. 7, in one embodiment, system 100 includes five microcolumn devices 10 connected to one another by a union connector 60, with one of the terminal microcolumn devices 10 further being connected to a terminal conduit connector 70 by a union connector 60. As shown in FIG. 8, in one embodiment, system 100 includes six microcolumn devices 10 connected to one another by a union connector 60, with one of the terminal microcolumn devices 10 further being connected to a terminal conduit connector 70 without the need for a union connector. The configurations shown in FIGS. 6-8 are only examples of various embodiments of the systems of the present invention, and are not meant to limit the scope of the systems, particularly with respect to the number of microcolumn devices included in the systems.

Figure 9:
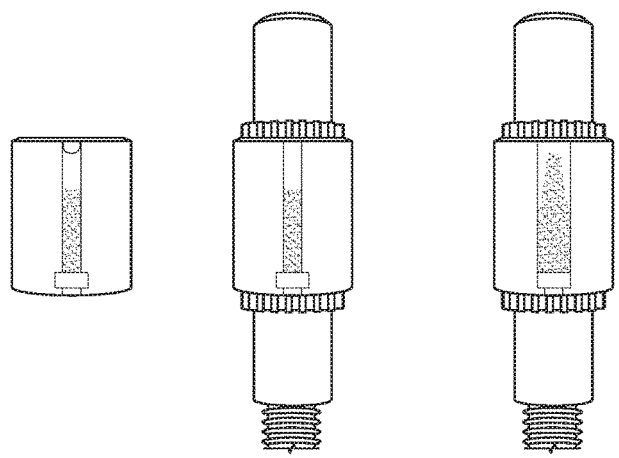
FIG. 9 is a photograph showing various aspects of embodiments of the microcolumn device of the present invention.
Figure 10:
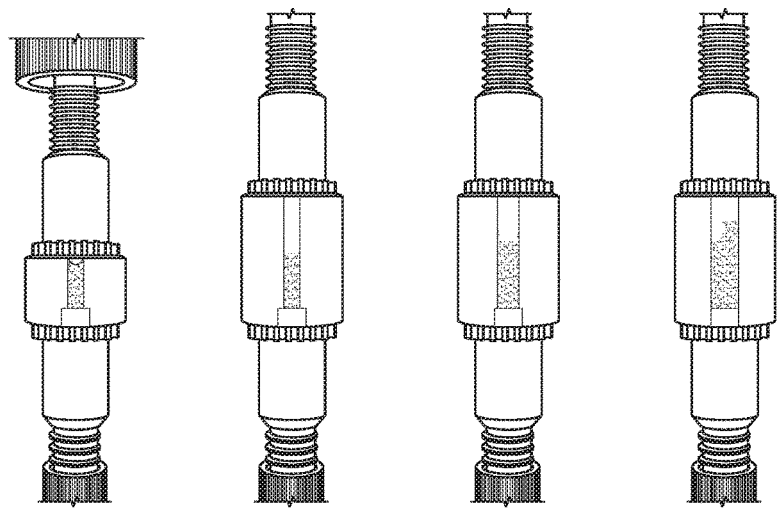
FIG. 10 is a photograph showing various aspects of embodiments of the microcolumn device of the present invention.

As shown in FIGS. 9-10, in various embodiments, the microfluidic devices of the present invention can be configured in different ways. Turning to the left side of FIG. 9, there is shown one embodiment of a body of a microcolumn device of the present invention, with the body having microfluidic channel that includes affinity chromatography resin. Turning to the middle and right side of FIG. 9, there is shown two embodiments of a microcolumn device of the present invention. As shown in FIG. 10, in various embodiments, each of the microcolumn devices can have different sized bodies and different amounts of affinity chromatography resin in the microfluidic channel. Further, as shown in FIG. 10, each microcolumn device can be connected at the top to a union connector.

FIG. 11 shows a schematic of one embodiment of a method of using the microcolumn devices and systems of the present invention for multiplexed selection of RNA aptamers. As shown in FIG. 11, the following steps can be followed for multiplexed selection of RNA aptamers: Step 1: The starting RNA library is dynamically loaded onto multiple microcolumn devices of the present invention that are connected in a serial configuration. Step 2: The microcolumn devices of the present invention are re-arranged into a parallel configuration and the subsequent cycles in the process are done independently but simultaneously. Step 3: Unbound and weakly bound RNAs are washed away. Step 4: The remaining bound RNAs are eluted from each column separately. Step 5: The RNA molecules are reverse transcribed into cDNA and, in Step 6, a small fraction is analyzed via qPCR. Step 7: The remaining cDNA is PCR amplified and then in Step 8 is transcribed back into RNA to make a new amplified pool for Step 9, the next selection round. The steps shown with dashed arrows in FIG. 11 are optional and are not necessarily done in each round.

EXAMPLES

The following examples are intended to illustrate particular embodiments of the present invention, but are by no means intended to limit the scope of the present invention.

Example 1

Multiplexed Microcolumn-Based Process for Efficient Selection of RNA Aptamers

Design and Fabrication of Micro-Column Devices

The micro-column devices were assembled using custom fabricated and commercially available parts. The internal component was made from a transparent biocompatible plastic. Each device has a flat recess in one end to hold a porous polymer frit which acts to retain the resin material in the device. A slightly smaller diameter hole along the remaining length of the device forms the actual column. By varying both the length and internal diameter of the column, we were able to make columns with a range of volumes from 2 to 50 µL. NanoPorts that accommodate standard plastic tubing connectors were bonded to either end of the column using cyanoacrylate adhesive. Overall this design minimizes the dead volume within the device.

The microcolumn device shown in FIG. 1 was fabricated from a ⅜" diameter poly(ethylene terephthalate glycol) (PETg) rod. The total rod length was 0.453" (11.5 mm) with a 1/16" (1.6 mm) diameter flat recess machined 0.060" (1.5 mm) deep to yield an available column length of 10 mm. The internal column diameter was of 0.043" (1.1 mm) which gave a total column volume of 10 µL. A male-male union connector can fit into either NanoPort connection and thus allows either multiple devices to be connected in series or to connect the device(s) to other laboratory equipment.

Micro-Column Based Selection and Amplification Steps

Small batch experiments were conducted to pre-immobilize the hexahistidine-tagged protein targets onto Ni-NTA affinity resin beads at a loading capacity of 0.6 µg protein/µL resin. Porous polymer frits were punched from larger discs using a 1.5 mm Biopsy punch and then inserted into the outlet side of the column that contained the flat recess feature. A standard 10-32 fluidic component (either terminal or union) was connected to the same side NanoPort and thus acted to hold the frit in place. A total of 10 µL of protein-loaded Ni-NTA resin was manually injected into the column space. The resin-filled micro-column devices were connected in a serial arrangement using male-male union connectors. The total pressure drop across this entire arrangement limits the number of micro-column devices that can be connected. In practice, typically anywhere between three and six devices are used, although any number of devices may be used according to the desired application.

As shown in FIGS. 2A-2B, our selections were performed using a multi-rack syringe pump to precisely control the volume and flow rate of solutions that were flowed through the micro-column devices. This also gave us the ability to program various steps, and to manipulate the dynamics and overall time of the selection process.

Figure 12:
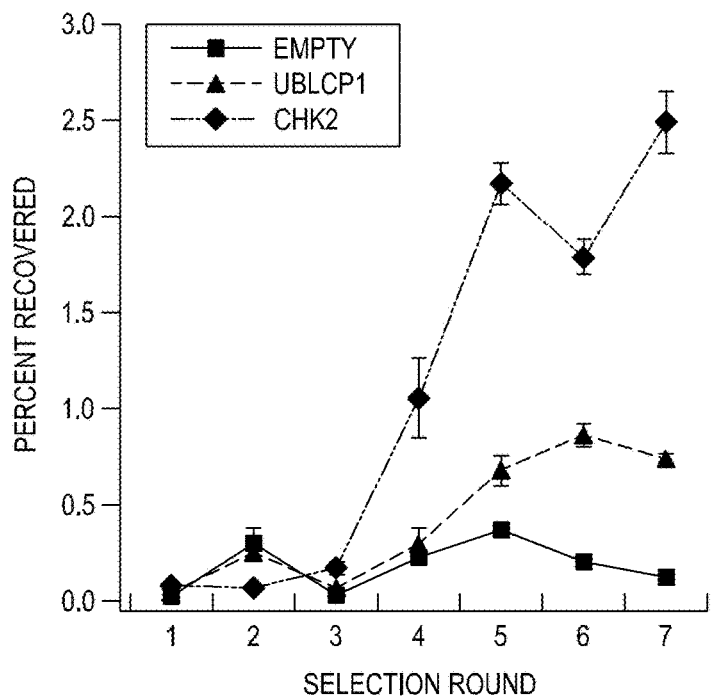
FIG. 12: Quantitative PCR results for the amount of RNA that was recovered from each micro-column device at different rounds. For Rounds 2 through 7, the micro-column devices were arranged in a parallel configuration for the loading step of the amplified RNA pools. The washing step flow rate was decreased from 3 mL/min (Rounds 1 and 2) to 0.3 mL/min (Rounds 3, 4, and 5) and finally to 0.03 mL/min (Rounds 6 & 7). For comparison, a completely empty micro-column was also included in the full set of experiments to discriminate the actual protein-target directed behavior from non-specific binding behavior.
Figure 13:
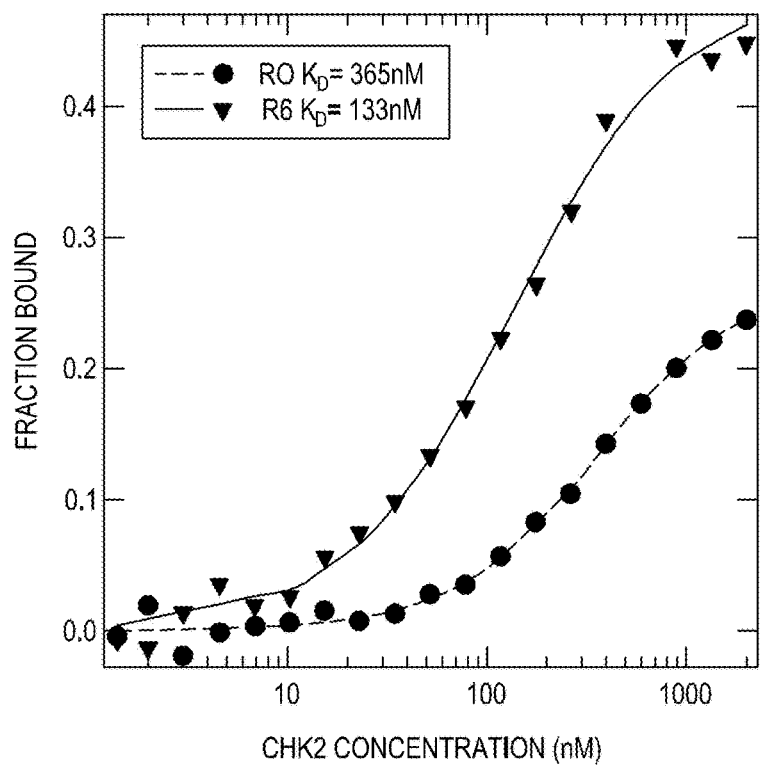
FIG. 13: Fluorescence electrophoretic mobility shift assay results for the starting RNA library (filled circles) and the Round 6 RNA pool with the CHK2 protein target.

The experimental results in FIGS. 12 and 13 were obtained for selections that were performed with three micro-column devices. One device was filled with UBLCP1 protein on Ni-NTA resin, another was filled with CHK2 protein on Ni-NTA resin. A completely empty micro-column was also included in the full set of experiments to discriminate the actual protein-target directed behavior from non-specific binding behavior. The devices were arranged in the following order:

INLET→Empty-UBLCP1-CHK2→OUTLET

To minimize any possible non-specific binding of the nucleic acid library, a blocking buffer that contained a high concentration of yeast tRNA molecules was pre-loaded onto the devices. Next, a 1 mL solution containing the random RNA library was injected onto the devices at a low flow rate (typically 1 to 10 µL/min) in order to give sufficient time for binding to occur onto the protein targets. Only the RNA molecules that did not bind to either the empty micro-column or the UBLCP1-loaded micro-column were introduced onto CHK2-loaded micro-column. Next, the devices were re-arranged into a parallel configuration and washed with binding buffer to remove any RNA molecules that were possibly bound to Ni-NTA sites on the resin bead surface that did not have protein bound. The volumes and flow rates in this step were used to vary the overall time and/or harshness of the wash in order to most effectively eliminate nonspecific or weakly bound RNA molecules. This separation also allows isolated and individualized treatments for different devices if needed. Finally, the RNA-target complexes were chemically stripped off of the surface of the resin beads by introducing an EDTA-containing buffer which specifically disrupts the attachment of the protein to the Ni-NTA site.

As shown in FIG. 11, the elution samples from individual micro-columns were processed to prepare a new pool of RNA molecules that contains many copies of only those molecules that bound to a particular target protein. The entire selection process was repeated by re-injecting the amplified pool back onto the same micro-column device filled with a fresh batch of target-loaded resin material. With each round of selection and amplification steps, the amplified RNA pool should exhibit a higher affinity for the specific protein target.

RNA aptamers for both protein targets were successfully selected from the starting library. The enrichment of the entire pool was assessed using two different techniques. Quantitative PCR (qPCR) measures both the total and relative amount of the input RNA library that was bound and recovered from the micro-column device in each selection round (see FIG. 12). An increase in recovery indicates preferential binding of the amplified pool onto the available target while no change in recovery indicates no preferential enhancement of the molecules that make up the pool. For the first three selection rounds, there is no difference in performance of the empty and target-loaded devices. However, for all subsequent rounds, the percent recovery on the CHK2 device is significantly higher than that observed for the empty device. After Round 5, the percent recovery on the UBLCP1 device is also different than the empty device. The affinity of the amplified pools for the specific target was quantified in a completely separate experiment known as a Fluorescence Electrophoretic Mobility Shift Assay (F-EMSA). A small amount of RNA is mixed with various amounts of the target and the fraction of target-bound RNA at the different target-protein ratios is evaluated by separating the products on an agarose gel. The fraction of target-bound RNA is plotted versus the amount of target and the data fit with theoretical binding models to determine the dissociation constant ($K_D$); $K_D$ values decrease as binding affinity increases. FIG. 13 clearly shows that amplified pool from Round 6 has a significantly lower $K_D$ value than that of the initial random RNA library for the CHK2 protein.

Finally, high-throughput sequencing of the amplified pools was performed to determine if specific aptamers were being enriched in the successive rounds of selection. This technique can yield several hundred million sequence samples from a single pool. This makes sequencing multiple pools simultaneously possible (by use of a barcode sequence to distinguish them). More importantly, the sensitivity of this technique can eliminate the need for many additional cycles that would be necessary for high affinity sequences to converge and dominate the pool. By taking advantage of both of these traits, it is also possible to look at behavior between selection rounds, providing a higher degree of confidence that sequences of interest demonstrate expected behavior, making use much more robust to possible biases in the pools or in the processing.

Table 1 shows the twenty sequences that were most prevalent (i.e., highest multiplicity values) in the amplified pool from Round 6 for the CHK2-loaded micro-column device. The results clearly show that these sequences were not present in the Round 3 pool (all zero multiplicity values) but were preferentially selected and enriched in the subsequent three rounds. These results are in good agreement with those from FIG. 16 that showed higher recoveries after Round 3. Most importantly, these sequences are unique to the CHK2 protein target—they were not present at all in the amplified pools from Round 6 for either the UBLCP1-loaded or the empty micro-column devices.

As shown in Table 1, the sequences contained therein correspond to SEQ ID NOs. according to the "Ranking" column on the left. In other words, the Ranking number assigned to each sequence in Table 1 also corresponds to the SEQ ID NO., i.e., Ranking number 1 corresponds to SEQ ID NO:1; Ranking number 2 corresponds to SEQ ID NO:2; Ranking number 3 corresponds to SEQ ID NO:3; Ranking number 4 corresponds to SEQ ID NO:4; Ranking number 5 corresponds to SEQ ID NO:5; Ranking number 6 corresponds to SEQ ID NO:6; Ranking number 7 corresponds to SEQ ID NO:7; Ranking number 8 corresponds to SEQ ID NO:8; Ranking number 9 corresponds to SEQ ID NO:9; Ranking number 10 corresponds to SEQ ID NO:10; Ranking number 11 corresponds to SEQ ID NO:11; Ranking number 12 corresponds to SEQ ID NO:12; Ranking number 13 corresponds to SEQ ID NO:13; Ranking number 14 corresponds to SEQ ID NO:14; Ranking number 15 corresponds to SEQ ID NO:15; Ranking number 16 corresponds to SEQ ID NO:16; Ranking number 17 corresponds to SEQ ID NO:17; Ranking number 18 corresponds to SEQ ID NO:18; Ranking number 19 corresponds to SEQ ID NO:19; and Ranking number 20 corresponds to SEQ ID NO:20.

TABLE 1

High-throughput sequencing results ranked according to the highest multiplicity values for the twenty sequences from the CHK2 round 6 amplified pool

| Rank-ing | Random region sequence | Multiplicity value | | | | | |
|---|---|---|---|---|---|---|---|
| | | R3_CHK2 | R4_CHK2 | R5_CHK2 | R6_CHK2 | R6_EMPTY | R6_UBLCP1 |
| 1 | ATTCGATCGGTTCCAACGCTCTGTCGCCTAAGTGAACAGATGAAGAAAAAATAGCCCAATAAGAGGCAACAA | 0 | 23 | 237 | 1378 | 0 | 0 |
| 2 | ATTCCAAGCCTTCACTCCGCAAAATACGCGCTTCCAAATAATAACAATAAGAACACCTAGGAAGCAACGCGC | 0 | 6 | 58 | 335 | 0 | 0 |
| 3 | ATTCCAACGAGATACAATAATAACAATAACCACCCCGATTCGTTCCGTGATCCATAAATCGAGCATGCACAC | 0 | 5 | 40 | 322 | 0 | 0 |
| 4 | ATTCACAAGCTTTATCCTAACAGCCAGAGACCTCACCACCCAGAGAAGAGCAGAGTTGCATAAGCAACCATG | 0 | 0 | 35 | 265 | 0 | 0 |
| 5 | ATTCATACACTTCATCACCCCAGAGCTGTGTTGCTGAAAGGCCTACCTACAGAGAAGAACAAGAGCCACCAG | 0 | 2 | 36 | 196 | 0 | 0 |
| 6 | ATTCCAGTCCTAGCACAAGACTGCAACGTGGATATGACCCCATACTGACTAACAATAACAACAAGGTAGGGA | 0 | 3 | 54 | 192 | 0 | 0 |
| 7 | ATTCCATACATTGCCCACGGCTCCGAGCGATAACCTGCAAACGCTCACTATCTAACAAAAGCAAAAACCTGT | 0 | 5 | 29 | 173 | 0 | 0 |
| 8 | ATTACTACCGTCCCACAATAATAATAACAACAAAGGGCGAGATTATTTCGTAACACTGGACCGACGAGTTTA | 0 | 5 | 32 | 170 | 0 | 0 |
| 9 | ATTCTTTCCGCCCTTCGCGTACTTAAGCCCATACCAGTGATCCGTATAAAAATAATAATAATAACCATCGGA | 0 | 8 | 31 | 166 | 0 | 0 |
| 10 | ATTCTCACCTACAACGCTTACCCAATCTTCGCCCAGTTGCGAATGGCTGAAGACCCGATAAGAGGTTGAGCC | 0 | 4 | 42 | 159 | 0 | 0 |
| 11 | ATTCATCCTAATATCCTAAAGTCGATCACTGAGCCAGCCTGGACCGATAACAACAACAACAAAGCGACTACT | 0 | 4 | 40 | 157 | 0 | 0 |
| 13 | ATTCATGACCAGTTCACCTTAGGTCTACGGCTAGGAATCTAGGATTAAATAATAATAACAACAAATTCCATC | 0 | 5 | 53 | 154 | 0 | 0 |
| 12 | ATTCCAAAGGCCACCTAGAAGCCAAACCAAAGAGAATCTACAGGACCCATACTCAGCATACAGAGAGCACTG | 0 | 6 | 30 | 154 | 0 | 0 |
| 14 | ATTCTCCCAACAGGAGACTTCGCACCCTCCATCTCCGAAAACTGCAAACAGGACATACAACAACAATAATAA | 0 | 12 | 51 | 144 | 0 | 0 |
| 15 | ATTCCGAGCCAAAGTCATAACCAACCAGTGATAATCCAACAGAGCCCAAACGCCAGCCATTAAGAGCAAACG | 0 | 3 | 24 | 138 | 0 | 0 |
| 16 | ATTCCCGGCTTTGTTACAAAATAGCGAAACGATAAGAGGGGAAAACCCCGCCGCCGCAATAAGACGACGTA | 0 | 3 | 12 | 132 | 0 | 0 |
| 17 | ATTCATAAACTCCTGTCAACAGTTCTGCAATGCATACGCATTACGCCATAATAACAATAATAAGAAGCGCGC | 0 | 3 | 34 | 128 | 0 | 0 |
| 18 | ATTCATTCGCACGATACCTACGTAAACTTTCCGAAGCAGGAACTATTTAGAAGCAGAAAAAACCAGCCACTT | 0 | 0 | 18 | 121 | 0 | 0 |
| 19 | ATCCACACAACACCAATAATAACCCATCTGAAATAGTCCCAATGTAAAAGCCAAGTGCGAAAACAAATTAGG | 0 | 4 | 28 | 118 | 0 | 0 |
| 20 | ATTCAGCATCGCCCACGGCGCTCCAGGTCGTATGACAGCATGTCCAATACAAAACCAATAACAACGAGGACA | 0 | 2 | 17 | 109 | 0 | 0 |

Example 2

Multiplexed Microcolumn-Based Process for Efficient Selection of RNA Aptamers

This example describes one embodiment of a reusable microcolumn and process for the efficient discovery of nucleic acid aptamers for multiple target molecules. The design of our device only requires microliter volumes of affinity chromatography resin—a condition that maximizes the enrichment of target-binding sequences over non-target (i.e. background) binding sequences. Furthermore, the modular design of the device accommodates a multiplex aptamer selection protocol. We optimized the selection process performance using microcolumns filled with Green Fluorescent Protein (GFP)-immobilized resin and monitoring, over a wide range of experimental conditions, the enrichment of a known GFP-binding RNA aptamer (GF-Papt) against a random RNA aptamer library. We validated the multiplex approach by monitoring the enrichment of GFPapt in de novo selection experiments with GFP and other protein preparations. After only three rounds of selection, the cumulative GFPapt enrichment on the GFP-loaded resin was greater than $10^8$ with no enrichment on the other non-specific targets. We used this optimized protocol to perform a multiplex selection to two human Heat Shock Factor (hHSF) proteins: hHSF1 and hHSF2. High-throughput sequencing was used to identify aptamers for each protein that were preferentially enriched in just three selection rounds, which were confirmed and isolated after five rounds. Gel shift and fluorescence polarization assays showed that each aptamer binds with high affinity ($K_D$<20 nM) to their respective targets. The combination of our microcolumns with a multiplex approach and high-throughput sequencing enables the selection of aptamers to multiple targets in a high-throughput and efficient manner.

As described in more detail below, we first evaluated the design space of our process using computer simulations of the binding kinetics of a model library over a wide range of experimental conditions. Next, we evaluated the performance of our microcolumns at those same conditions by monitoring the behavior of a known RNA aptamer (GFPapt) that binds tightly to Green Fluorescent Protein (GFP) and its derivatives (Ref. 14). Our results show that predictions based on simple kinetics fail to reproduce the behavior of low affinity binders under flow, suggesting that typical SELEX processes based on theoretical kinetics are likely to be far from optimal. Furthermore, we observed the best performances at protein concentrations 100 times less than the capacity of the resin. We also empirically validated a multiplex approach by monitoring the enrichment of GFPapt in de novo selection experiments with GFP, two non-related protein preparations, and an empty microcolumn. To examine the utility of our device, multiplex and 'in-line' negative selections were performed on two human Heat Shock Factor (hHSF) proteins: hHSF1 and hHSF2. High-throughput sequencing was used to identify enriched candidate aptamer sequences for hHSF1 and hHSF2. Fluorescence electrophoretic mobility shift assays (F-EMSA) as well as fluorescence polarization (FP) confirmed the selection of novel high affinity aptamers for hHSF1 and hHSF2.

Materials and Methods

Selection Simulations

Computational simulations were performed with a custom-made Matlab routine to test a wide variety of experimental parameters. The differential equations of association and dissociation kinetics (first-order with respect to each species) were numerically integrated with respect to time, distance along the microfluidic channel, and each aptamer type within the modeled library. Additional details are provided in Example 3

Preparation of Protein-Immobilized Resins

For each selection round a fresh batch of protein-bound resin was prepared. Ni-NTA Superflow or Glutathione-agarose resins were extensively washed with binding buffer (Ni-NTA binding buffer: 25 mM Tris pH 8.0, 100 mM NaCl, 25 mM KCl, 5 mM $MgCl_2$; Glutathione binding buffer: 10 mM HEPES-KOH pH 7.6, 125 mM NaCl, 25 mM KCl, 1 mM $MgCl_2$, 0.02% Tween-20) to remove any residual storage components. Hexahistidine- or GST-tagged proteins were prepared as described in Example 3 and immobilized onto the washed resin at 4° C. with constant mixing. The protein-bound resin was then degassed in a vacuum desiccator for approximately 20 min and carefully pipetted into the device (FIG. 1).

Nucleic Acid Library and GFP-Binding Aptamer

A random library containing ~$5 \times 10^{15}$ sequences of 120-nucleotide (nt) DNA templates was chemically synthesized by GenScript. It consists of a 70-nt random region flanked by two constant regions as described elsewhere (Ref. 15). The GFP binding RNA aptamer used in this work was previously identified as AP3-1 and characterized elsewhere (Ref. 14). Details on the library preparation and oligos used in this work are provided in Example 3.

Microcolumn Selection and Amplification Protocol

All of the solutions were degassed prior to use, and introduced into the microcolumns using a standard syringe pump (Harvard Apparatus). First, yeast tRNA (Invitrogen) in binding buffer was introduced to block any possible non-specific RNA binding sites. For each loading step, the RNA library was diluted in 1 mL of RNase-free binding buffer, heat-denatured at 60° C. for 5 mins, renatured by cooling down to room temperature while degassing, and then spiked with 200 U of RNase inhibitor (Invitrogen). A 10 µL aliquot was collected and used as a standard for the qPCR analysis. Each device was then washed with 3 mL of binding buffer (supplemented with 10 mM imidazole for selections with Ni-NTA resin) to remove unbound RNA. Finally, the RNA-protein complexes were eluted from individual microcolumns by flowing elution buffer (binding buffer+50 mM EDTA) at a rate of 50 µL/min for 6 mins. Eluted RNA and the input samples were phenol:chloroform extracted, ethanol precipitated together with 1 µL of GlycoBlue (Ambion) and 40 µg of yeast tRNA (Invitrogen), and the resulting pellet was re-suspended in RNase-free water.

Both the re-suspended pools and standards were reverse transcribed with MMLV-RT enzyme. For the optimization experiments, ~10% of the selected pool and the input sample were reverse transcribed in a separate reaction for GFPapt quantitation. Residual RNA was eliminated by treating the samples with RNaseH (Ambion). A small amount (less than 5%) of the cDNA products were analyzed on a LightCycler 480 qPCR instrument (Roche) to determine the amount of RNA library and GFPapt that was retained on each device. Two different sets of oligos (see Example 3 for details) were used to independently evaluate the amount of the RNA library/pool and GFPapt, respectively. The cDNA samples from each round were PCR amplified then subjected to phenol:chloroform and chloroform extractions, and a final purification step using DNA Clean & Concentrator (Zymo Research) spin columns. A fraction of the purified PCR product was used to make the RNA pool for the next round of SELEX. A typical 72 µL transcription reaction consisted of 500 ng of DNA, 546 pmol of each rNTP (Sigma), T7 RNA polymerase, 72 U RNase inhibitor (Invitrogen), and 0.12 U yeast inorganic pyrophosphatase (NEB). The reactions were incubated at 37° C. for various times depending on the desired amount of RNA for the next selection round. The resulting RNA pool was DNaseI (Invitrogen) treated to remove the template DNA, verified by denaturing PAGE for length and purity, and finally quantified by Qubit BR RNA assay (Invitrogen).

High-Throughput Sequencing

A small amount of the purified PCR product from each target pool for various selection rounds (e.g., hHSF1 Round 5) were PCR amplified using primers that contain a unique 6 nt barcode and the necessary adapters for the HiSeq 2000 (Illumina) sequencing platform. Sequences of the primers and the barcodes are available upon request. Additional details on the sequencing data filtering and clustering analyses are given in Example 3.

Fluorescence Electrophoretic Mobility Shift Assay (F-EMSA)

Candidate aptamer sequences were amplified from the final Round 5 pool and prepared from sequence verified plasmid constructs (see Example 3). The candidate aptamers were 3'-end labeled with fluorescein 5-thiosemicarbazide (Invitrogen) as described previously (Ref. 16). 50 µL binding reactions were prepared with 2 nM fluorescently-labeled RNA and decreasing amounts of protein (2000 to 0 nM) in binding buffer containing 0.01% IGEPAL CA630, 10 µg/ml tRNA, and 3 U of SUPERase•In RNase Inhibitor (Invitrogen). Reactions were incubated at room temperature for 2 hours, spiked with 6×loading dye, and then loaded into the wells of a refrigerated 1.5% agarose gel prepared with 0.5×TBE, 1 mM $MgCl_2$ buffer. The gel was run for 80 minutes at 100 volts in refrigerated 0.5×TBE. Images were acquired using the fluorescein scan settings on a Typhoon 9400 imager (GE Healthcare Life Sciences). The resulting bands were quantified with ImageQuant software and the data was fit to the Hill equation using Igor (Wavemetrics) to estimate the equilibrium dissociation constant ($K_D$).

Results

Fabrication of Microcolumns for Selection of Aptamers

Our microcolumns were assembled using both custom fabricated and commercially available parts. The column consists of a transparent bio-compatible plastic rod fitted with a porous frit that retains the resin in the device (FIG. 1). By varying both the length and internal diameter of the column, we were able to fabricate columns with a range of volume capacities from 2 to 50 µL. NanoPorts (IDEX Health & Science) that accommodate standard tubing connectors were bonded to either end of the column. Overall, this design has a number of important features: simple union connectors can be used to arrange multiple microcolumns into various configurations, the 'dead volume' between the devices is minimized and is generally less than 1 µL, and they can be connected to common laboratory equipment to automate the selection steps. To perform the multiple target aptamer selection, we developed a workflow process wherein a set of microcolumns, each pre-filled with a different target-immobilized resin, are arranged into a serial configuration (FIG. 11). With our pump system a typical arrangement could contain up to ten parallelized assemblies of devices, but the general approach can easily be scaled up for a larger number of parallel processes. A single aliquot of the starting random library is then flowed through these devices allowing the target binding aptamers to be captured on the resin within each individual column. The library molecules that do not bind to any target are discarded and then the individual microcolumns are disconnected and reorganized into a parallel configuration (FIG. 11). This arrangement allows for specific elutions from each target and thus separate processing of only the bound sequences to create target-specific amplified pools for the next selection round. Note that following reverse transcription of the RNA aptamer into cDNA, we used quantitative PCR (qPCR) to determine the amount of nucleic acid recovered from each device. This information was used to determine the optimal number of PCR cycles and thus minimize the chance of amplification artifacts (Ref. 17). Although FIG. 11 shows the microcolumns arranged exclusively in a parallel configuration after the first selection round, it is also possible to use a serial configuration in later rounds. This arrangement would allow for negative or counter selections to be done simultaneously with the selection step to enhance specificity for the target.

Figure 14:
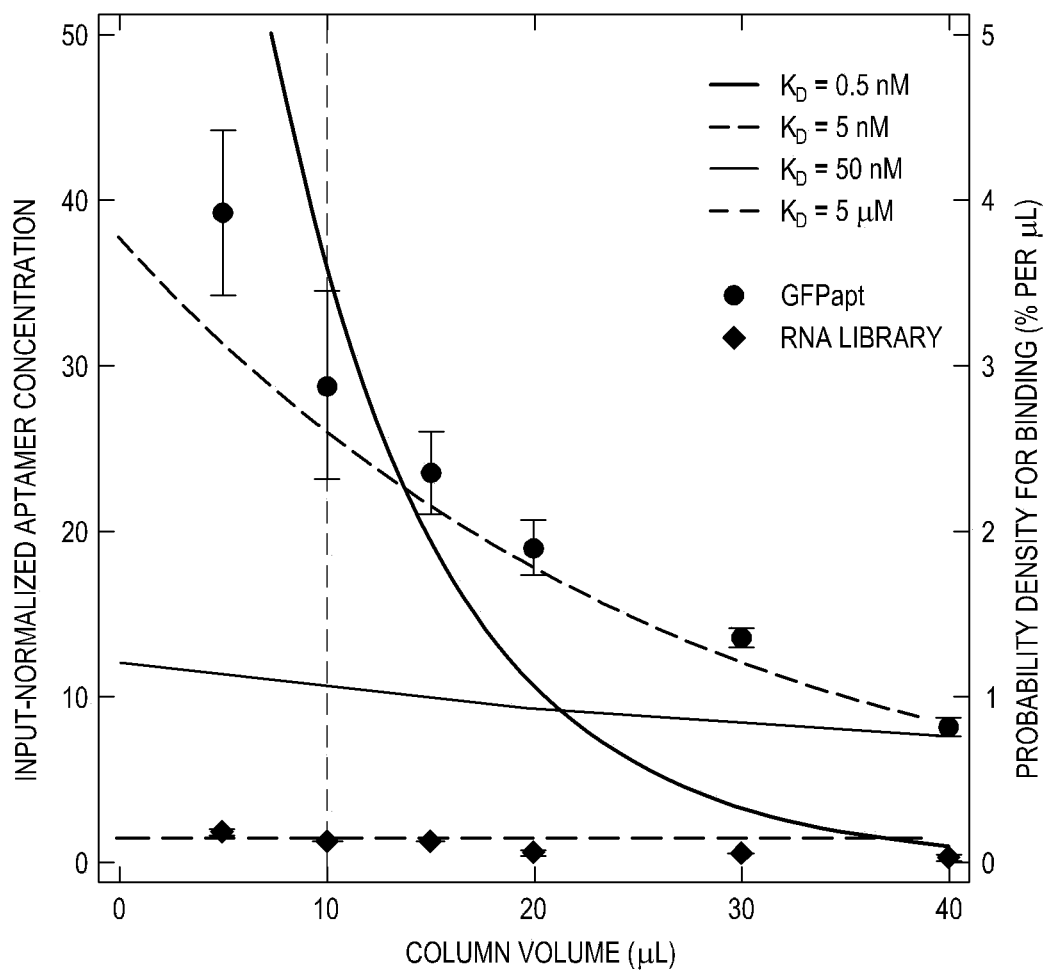
FIG. 14. Dependence of aptamer recovery on microcolumn volume. Solid and dashed-lines are the simulation results for the input-normalized concentrations of aptamers with various binding affinities ($K_D$ ranging from 0.5 nM to 5 μM) as a function of microcolumn volume. Data points are the experimentally measured binding densities, given as percent of the total, of high-affinity GFPapt (green filled circles) and low-affinity, non-specific binding N70 random library (red filled diamonds) as a function of microcolumn volume. Input-normalized aptamer concentrations are defined as the bound aptamer concentration at a point along the column divided by the initial aptamer concentration. Probability densities for binding are defined as the probability per unit volume for molecules to bind in the vicinity at a point along the column. The two y-axes are related by the total loaded sample volume. The dashed vertical line at 10 μL marks the volume of the devices used for the optimization experiments.

The size of our microcolumns was chosen for primarily two reasons. First, they are small enough that they require only small amounts of material for each selection round, yet their internal dimensions are sufficiently large enough that they could be easily filled with a variety of different resins. Second, we simulated the binding kinetics of a model library binding to a model target molecule within our device and discovered that aptamers with strong binding affinities for the target (i.e. equilibrium dissociation constant $K_D$=0.5 nM) were preferentially retained at the input end (i.e., in the first few microliters) of the microfluidic column (FIG. 14). Aptamers with weaker binding affinities for the target ($K_D \geq 50$ nM) were distributed almost uniformly throughout the microfluidic column with concentrations nearly identical to the input concentration. Therefore, smaller columns increase the mean density of strong binders, a condition that would require fewer selection rounds to identify aptamer candidates. A previous study used an affinity capillary column that was physically cut into smaller pieces to isolate the highest affinity aptamers in the earliest column segments (Ref. 18).

We evaluated experimentally the binding distribution of an RNA aptamer, hereafter referred to as GFPapt, on microcolumns that were filled with various amounts of GFP-immobilized resin. It had been previously shown that this aptamer has a strong binding affinity ($K_D \sim 5$ nM) for GFP (Ref. 14) and thus serves as a model molecule for the high-affinity target-binding aptamers that are presumed to be present in random libraries. In order to determine the amount of non-specific, low-affinity (i.e., 'background') binding within the microcolumn, a small amount of the random RNA library (~5 pmol) was included in addition to the GFPapt (0.064 pmol). We used 0.6 µg of GFP per µL resin, binding and washing flow-rates of 100 µL/min, and qPCR assays to quantify the amount of both the GFPapt and the random library captured on the microcolumn. The experimental results are shown in FIG. 14 as a percentage density of the amount of both the GFPapt and the N70 random library loaded onto the device. The experimental results are well fit by the simulations for both high-affinity ($K_D$=5 nM for GFPapt) and low-affinity ($K_D \geq 10$ µM for the N70 random library) binding.

Optimization of Aptamer Selection Conditions

Figure 15A:
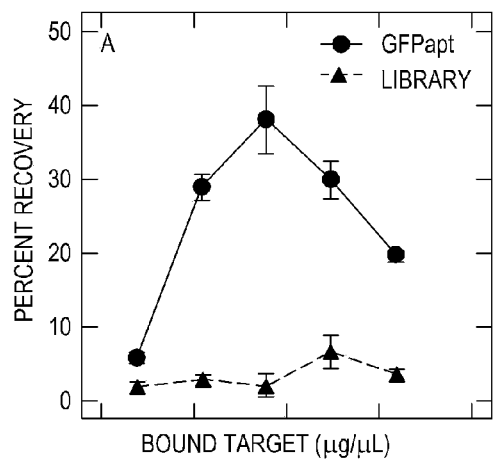
FIGS. 15A-15D. Optimization of microcolumn-based selection. Percent recovery of GFPapt (green) and the N70 random library (red) (FIG. 15A) and the GFPapt enrichment (FIG. 15B) for different amounts of GFP immobilized onto Ni-NTA resin in a 10 μL microcolumn; loading and washing flow rates were 100 μL/min. Percent recovery of GFPapt (green) and the N70 random library (red) (FIG. 15C) and the GFPapt enrichment (FIG. 15D) for different flow rates; the amount of GFP immobilized onto Ni-NTA resin was 0.6 μg/μL. The solid lines show the effect of the loading flow rate at a fixed washing flow rate of 100 μL/min while the dashed lines show the effect of the washing flow rate at a fixed loading flow rate of 100 μL/min. The error bars represent the standard deviation of triplicate experiments and measurements at each condition.
Figure 15C:
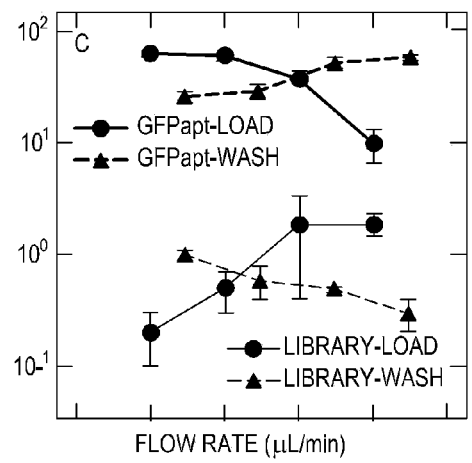
Figure 15B:
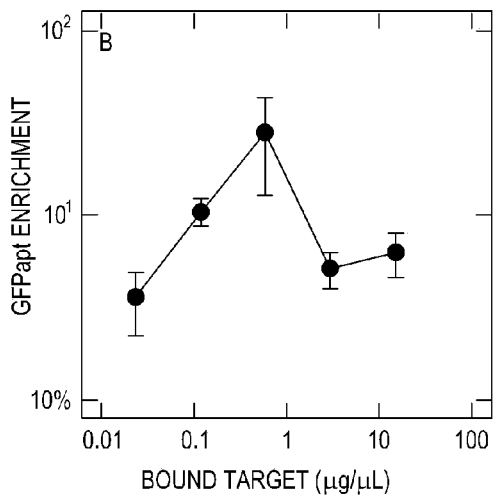
Figure 15D:
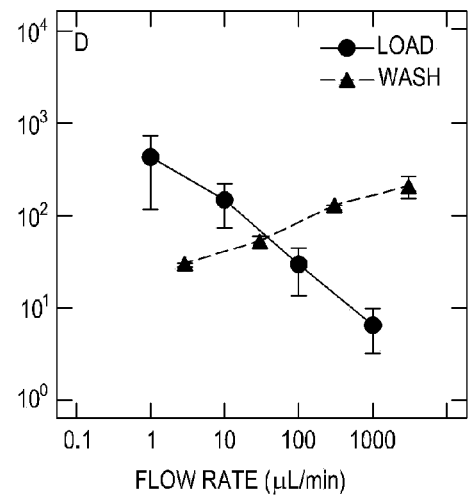

To optimize the performance of our devices and to further test our simulation predictions, we used microcolumns filled with GFP-immobilized Ni-NTA resin to evaluate the binding behavior of GFPapt and the random N70 library over a wide range of experimental conditions. The results are shown as a percentage of the amount loaded onto the device (FIGS. 15A and 15C). For each condition, the GFPapt enrichment was calculated as the ratio of the percent amounts of GFPapt to random library (FIGS. 15B and 15D).

Figure 18A:
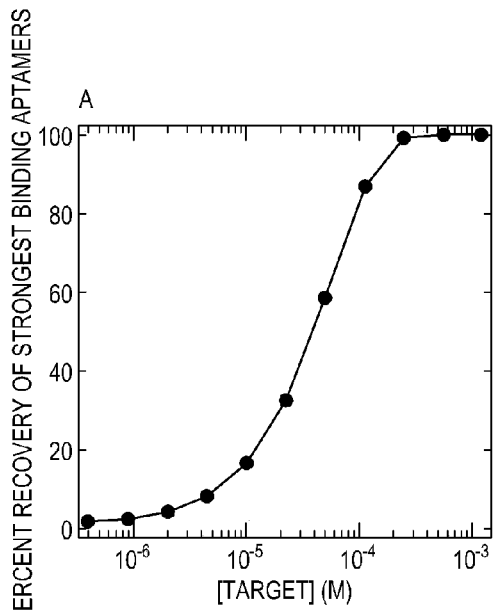
FIGS. 18A-18B. Simulation results for the effect of target protein concentration on percent recovery of a strong binding aptamer ($K_D$=5 nM) (FIG. 18A) and random library molecules (FIG. 18B). The other simulation parameters were total resin volume=10 μL, loading flow rate=100 μL/min, and washing flow rate=100 μL/min.
Figure 18B:
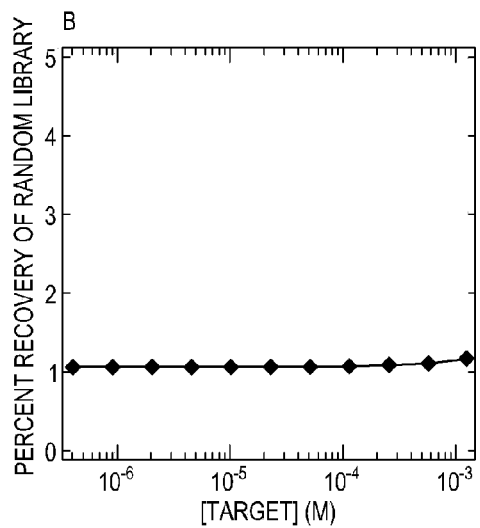

Affinity chromatography resins were developed primarily for protein purification applications and thus are capable of binding relatively large amounts of target molecules—the reported binding capacity of the resin used in our experiments is 20 to 50 µg of protein per µL of resin. Despite the widespread use of these resins for aptamer selections, there is no information available on how this parameter affects the selection performance, since none of the previous studies optimized the resin binding conditions (Ref. 7). In order to determine the optimum amount of bound target, we prepared five different batches of resin with varying amounts of immobilized GFP, from 0.024 to 15 µg of protein per µL of resin in 5-fold increments. The amount of GFPapt captured within the device was strongly dependent on the amount of GFP target on the resin (FIG. 15A). Interestingly, we found that the highest recovery (~40%) was obtained at the intermediate value of 0.6 µg of protein per µL of resin (~15 µM). Library recovery was essentially independent of the amount of target and so the GFPapt enrichment was also maximized at the same intermediate value (FIG. 15B). We had initially hypothesized that saturating the resin with GFP would maximize the number of target binding aptamer molecules while also minimizing non-specific binding sites on the resin surface, yielding the highest GFPapt enrichment. Kinetic simulations done using a similar approach to that described for determining the optimal device size, except with a higher fraction of strong-binding aptamers (~1%) to match the experimental conditions, correctly predicted that there was no effect of target amount on recovery of the random library (FIG. 18). However, the simulations predicted that the highest recovery of the strong-binding aptamer would occur at the conditions with the highest amount of bound target (FIG. 18). We believe that this discrepancy between our experimental observations and simulation results is primarily due to steric hindrance where macromolecular crowding effects on the resin surface decreases the binding affinity of the specific aptamer sequence—a similar phenomenon has been reported for the binding of soluble proteins to surface lipid vesicles (Ref. 19). The formation of the aptamer-target complex could also hinder the binding of other aptamer molecules. Our results support using concentrations below a critical packing density that is determined by the larger of the two bio-molecules. All of the subsequent optimization experiments were conducted using resin prepared at the optimum value of 0.6 µg of protein per µL of resin.

Figure 19A:
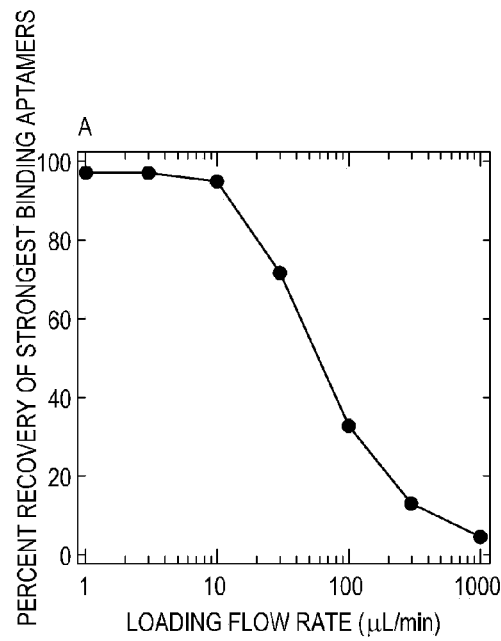
FIGS. 19A-19B. Simulation results for the effect of loading flow rate on percent recovery of a strong binding aptamer ($K_D$=5 μM) (FIG. 19A) and random library molecules (FIG. 19B). The other simulation parameters were total resin volume=10 μL, concentration of immobilized target protein=22 μM, and washing flow rate=100 μL/min.
Figure 19B:
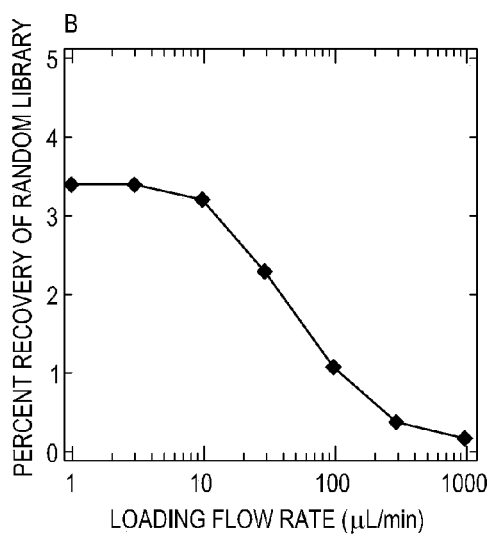
Figure 22A:
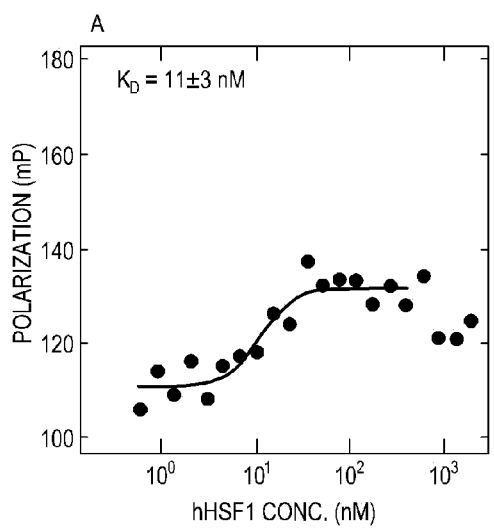
FIGS. 22A-22D. Fluorescence polarization (FP) assay results for binding of hHSF1-R5-1 aptamer to GST-hHSF1 (FIG. 22A), GST-hHSF2 (FIG. 22B), hexahistidine-dHSF (FIG. 22C), and GST-tag (FIG. 22D). The solid line in each panel (except D) is the best-fit of the Hill equation to the experimental data with the given $K_D$ value.
Figure 22B:
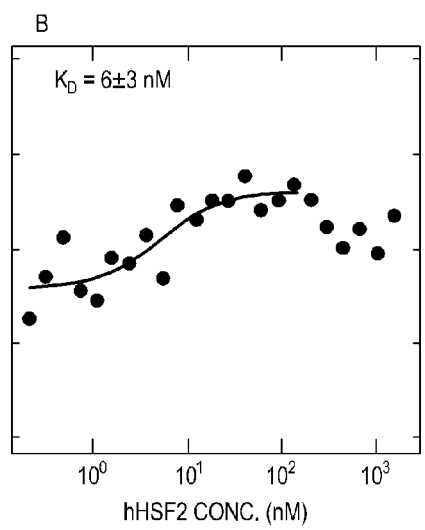
Figure 22C:
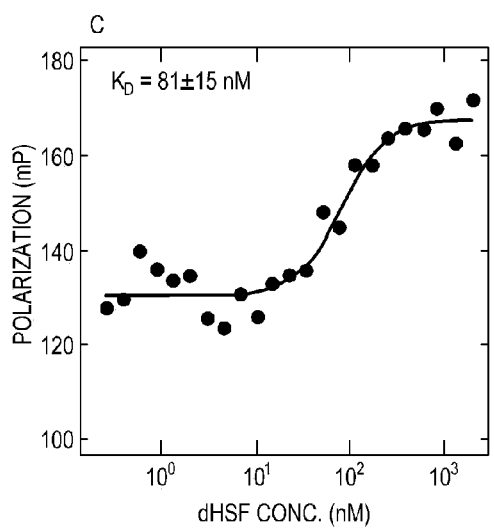
Figure 22D:
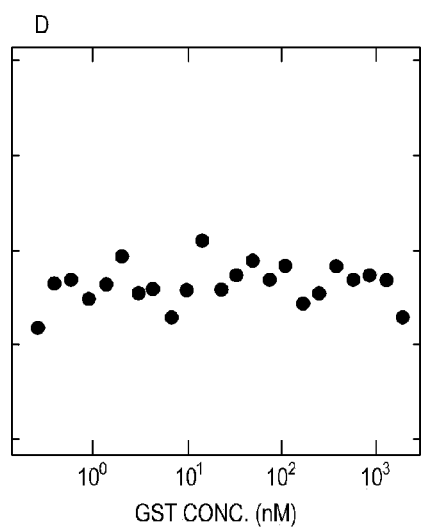

It is well known that the best affinity chromatography performance is realized when the loading step is operated at the lowest possible flow rates to approach equilibrium conditions. However, there is a practical limitation to the experiment time. In order to determine the optimum condition, while also keeping within a practical experimental timeline, we varied the loading flow rate from 1 to 1000 µL/min. The recoveries of GFPapt and library were both strongly dependent on the flow rate but with considerably different trends (FIG. 15C). At the lowest flow rate, we observed the highest GFPapt recovery, the lowest library recovery, and thus the best GFPapt enrichment. By operating the process at higher flow rates, we observed a gradual decrease in performance as measured by a decrease in GFPapt enrichment (FIG. 15D). Our kinetic simulations correctly predicted that the highest recovery of the strong-binding GFPapt molecule would be obtained at the lowest flow rate (FIG. 19). However, the simulations also predicted the same trend of decreasing recovery with increasing loading flow rate for the random library (FIG. 19). This disagreement between simulation and experimental results for the library is discussed below.

After completing the loading step, a fixed-volume washing step was employed to improve the separation performance by removing any unbound or weakly bound sequences. We varied the washing flow rate from 3 µL/min to 3 mL/min. We observed similar results to those seen before in that the recoveries of both GFPapt and library had different trends with increasing flow rate. Whereas the GFPapt recovery increased at higher flow rates, the library recovery decreased (FIG. 15C). Thus, the best GFPapt enrichment was obtained at the highest washing flow rate (FIG. 15D). Together, all of the optimization experiments enabled us to choose the optimal experimental conditions that maximize the enrichment of strong-binding aptamers for each selection round, while keeping within practical experimental and time constraints. These conditions are particularly important for the earliest selection rounds when there are only a few copies of each aptamer sequence. Our results also revealed the importance of empirical validation and characterization of different selection conditions, since the kinetic simulations were unable to properly predict all the experimental trends. For example, simulation results for the washing step predicted a gradual increase in the recovery of random library (FIG. 20)—the exact opposite trend to that seen experimentally. In our simulations, the behavior of each species was determined by the on-rate and off-rate kinetic constants. They do not include other phenomena such as shear or pressure-related flow effects that could preferentially affect the behavior of weak-binders and the ultimate separation performance of our microcolumns.

After fully characterizing the operating conditions to maximize the enrichment of strongly binding aptamers in our microcolumns, we then proceeded to validate our selection strategy empirically by monitoring the enrichment of GFPapt molecules in de novo selections with multiple protein targets, including GFP. For each round, three microcolumns were filled with Ni-NTA resin that had been pre-immobilized with either GFP or two unrelated proteins: CHK2 and UBLCP1. The latter two were chosen, because they have similar size and charge properties to the specific target GFP and were readily available with hexahistidine affinity tags (Table 2). An empty microcolumn was also included as a control to enable us to discriminate target-binding from device bias.

TABLE 2

Properties of the target proteins

| Protein | Molecular Weight (kDa) | Isoelectric Point | Affinity tag |
|---|---|---|---|
| GFP | 27 | 5.5 | Hexahistidine (N-terminus) |
| UBLCP1 | 37 | 6.1 | Hexahistidine (C-terminus) |
| CHK2 | 61 | 5.6 | Hexahistidine (N-terminus) |
| hHSF1 | 86 | 5.3 | GST* (N-terminus) |
| hHSF2 | 88 | 4.9 | GST*(N-terminus) |
| dHSF | 80 | 4.9 | Hexahistidine (N-terminus) |

*GST tag ~30 kDa

Figure 16:
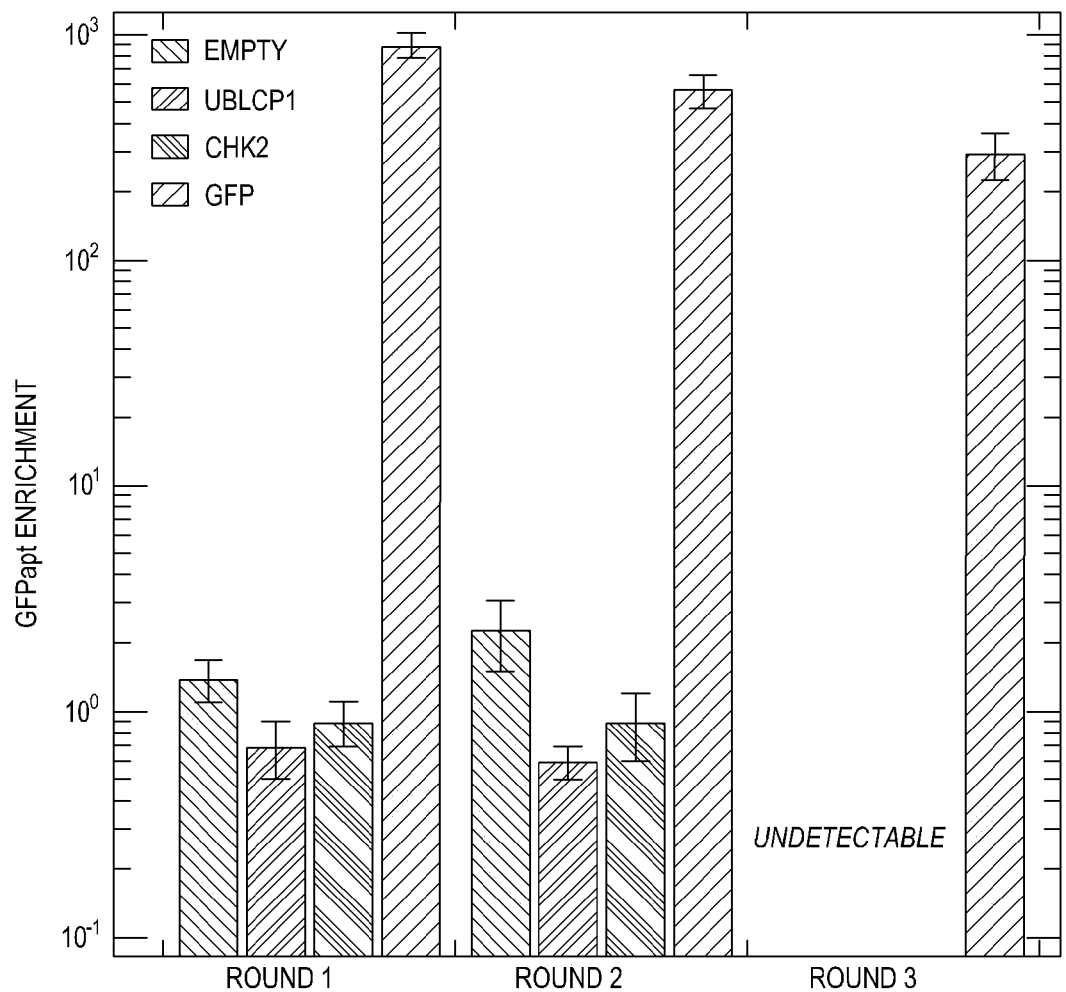
FIG. 16. Validation of specific aptamer-target enrichment for multiplex SELEX. UBLCP1, CHK2, and GFP were pre-immobilized on Ni-NTA resin at a density of 0.6 μg protein per μL resin and an empty microcolumn was also included as a control. The loading flow rate for all the rounds was 1 μL/min. The enrichment of GFPapt was monitored on all four microcolumns for three consecutive selection rounds. The results are presented in the same order that the four devices were arranged in the serial configuration used in Round 1. The GFPapt enrichment was calculated as the ratio of the percent amounts of GFPapt to random library. The error bars represent the standard deviation of triplicate measurements for each microcolumn.

For the first selection round, four devices were arranged in a serial configuration in the following order: Empty, UBLCP1, CHK2, GFP. The GFP target was put at the end so that all of the GFPapt molecules that were combined with the random RNA library would have an opportunity to bind to the other targets; the loading solution for the first selection round contained 40 nmoles of the random RNA library (~5 copies of each sequence in the 5×10$^{15}$ library) and 6.4 fmoles of GFPapt in 1 mL of binding buffer. Thus, the initial molar ratio of library to GFPapt molecules was greater than six million to one. The enrichment of the GFPapt was determined for each microcolumn from qPCR analyses of the eluted samples (FIG. 16). Only the microcolumn filled with GFP-loaded resin showed significant GFPapt enrichment. In the first round, the recoveries of the GFPapt and the random library were 20% and 0.022% of the corresponding inputs, respectively, yielding a GFPapt enrichment of approximately 900-fold. However, for the other three devices, the GFPapt enrichments were all near unity indicating that there was no affinity for GFPapt over the random library. To decrease the material used in the selections, for the next two rounds the amount of the amplified RNA pool loaded onto each device was decreased by 20-fold from the amount used in the previous round. An appropriate amount of GFPapt was 'spiked-in' with the amplified RNA pool to maintain the same molar ratio that was recovered in the previous round. After Round 3, the amounts of GFPapt that were recovered on the three non-GFP devices were well below the qPCR detection limit; and therefore, no GFPapt enrichment results could be obtained. However, for the GFP device the GFPapt enrichments were much greater than 100-fold per selection round giving rise to a cumulative enrichment of over $10^8$-fold. At the end of Round 3, approximately 95% of the GFP selected pool was comprised of the GFPapt.

Microcolumn SELEX for hHSF Proteins

To conclusively demonstrate the multiplex utility of the microcolumns, we performed multiplex SELEX for a set of GST-tagged proteins: hHSF1, hHSF2, and four other related proteins. hHSF1 and hHSF2 are transcription factors that regulate stress response, including heat shock in human cells, and they also play a critical role during tumor formation and maintenance (Ref. 20). However, important questions remain unanswered regarding its molecular interaction and the specific mechanisms that are used to execute its functions. An RNA aptamer against the *D. melanogaster* HSF (dHSF) has been selected previously and used to inhibit the binding and recruitment of dHSF to the promoters of Heat Shock genes (Refs. 21 and 22). However, only moderate cross-reactivity with the hHSF proteins limit the use of this aptamer in functional studies in human cells (Ref. 23). Given the biological importance of HSF, we decided to select for aptamers directly to hHSF1 and hHSF2, which can be used as inhibitory tools to dissect the mechanisms of actions of these proteins.

Each protein was pre-immobilized onto Glutathione-agarose resin at approximately 1 μg of protein per μL of resin. The GST-tag was also included as a control and thus seven 20 μL microcolumns were arranged in a serial configuration for Round 1. Following the procedure outlined above, another aliquot of the starting RNA library (~5 copies of each sequence in the $5\times10^{15}$ library) was loaded onto the seven-microcolumn assembly and then separated into a parallel arrangement for all the subsequent rounds.

A total of five selection rounds were completed. For Rounds 2 through 5, 'in-line' negative selections were done by connecting a 10 μL microcolumn filled with GST-immobilized resin to the inlet of each of the six microcolumns for the GST-tagged proteins. These pre-columns were removed after the loading step for the subsequent wash and elution of the target protein-bound aptamers from each microcolumn.

We analyzed the sequences from the RNA pools from Rounds 3 and 5 for both hHSF1 and hHSF2 using high-throughput sequencing (Refs. 24 and 25). The total number of sequencing reads per pool ranged from 6 to 9 million. For both proteins, there was a noticeable shift towards higher multiplicity values from Round 3 to 5. In Round 3, the top twenty highest multiplicity sequences for each protein represented only ~0.04% of the total pool. However, in Round 5, the top twenty sequences represented 85.0% and 76.5% of the hHSF1 and hHSF2 selected pools, respectively (Table 3). In addition, of the top twenty highest multiplicity sequences in Round 3, between a quarter and a half of them were also among the top twenty highest multiplicity sequences in Round 5 for hHSF2 and hHSF1. The detection of enriched candidate aptamer sequences in earlier selection rounds was possible because of the high-throughput sequencing, which allowed us to select candidate aptamers for subsequent analysis.

We decided to investigate the potential binding of one of the top candidate sequences for hHSF1 and hHSF2. We chose the highest ranked sequences from the Round 5 pools that were also highly ranked in Round 3. For hHSF1, this was the $1^{st}$ ranked sequence in Round 5, hereafter referred to as hHSF1-R5-1, and also the $11^{th}$ ranked sequence in Round 3 (Table 3). For hHSF2, this was the $2^{nd}$ ranked sequence in Round 5, hereafter referred to as hHSF2-R5-2, and also the $6^{th}$ ranked sequence in Round 3 (Table 3). The full-length sequences and predicted structures of these two aptamer candidates are available in Example 3 (FIG. 21). These two candidates represented 13.4% and 6.8% of the corresponding Round 5 pools. The full-length aptamer candidates (including the constant regions) were PCR amplified from their respective pools using a candidate specific forward oligo and the reverse constant region oligo, and then cloned into plasmid vectors to obtain a pure template.

TABLE 3

| | hHSF1 Sequencing Results (per 10 Million Reads) | | | hHSF2 Sequencing Results (per 10 Million Reads) | | |
|---|---|---|---|---|---|---|
| ID | Round 5 Multi-plicity | Round 3 Rank | Round 3 Multi-plicity | ID | Round 5 Multi-plicity | Round 3 Rank | Round 3 Multi-plicity |
| hHSF1-R5-1 | 1340479 | 11 | 133 | hHSF2-R5-1 | 1627399 | 51 | 87 |
| hHSF1-R5-2 | 1274151 | 9 | 152 | hHSF2-R5-2 | 682671 | 6 | 205 |
| hHSF1-R5-3 | 1261696 | 6 | 190 | hHSF2-R5-3 | 660708 | 47 | 93 |
| hHSF1-R5-4 | 621764 | 22 | 98 | hHSF2-R5-4 | 569105 | 33 | 103 |
| hHSF1-R5-5 | 550234 | 54 | 55 | hHSF2-R5-5 | 567516 | 511 | 27 |
| hHSF1-R5-6 | 530607 | 24 | 93 | hHSF2-R5-6 | 558955 | 49 | 89 |
| hHSF1-R5-7 | 469695 | 3 | 164 | hHSF2-R5-7 | 485019 | 342 | 33 |
| hHSF1-R5-8 | 405537 | 30 | 79 | hHSF2-R5-8 | 384008 | 9 | 197 |
| hHSF1-R5-9 | 358828 | 7 | 165 | hHSF2-R5-9 | 370668 | 69 | 73 |
| hHSF1-R5-10 | 272611 | 27 | 84 | hHSF2-R5-10 | 304918 | 93 | 64 |
| hHSF1-R5-11 | 271480 | 10 | 147 | hHSF2-R5-11 | 225959 | 295 | 36 |
| hHSF1-R5-12 | 191659 | 1 | 500 | hHSF2-R5-12 | 212557 | 116 | 59 |

TABLE 3-continued

| | hHSF1 Sequencing Results (per 10 Million Reads) | | | | hHSF2 Sequencing Results (per 10 Million Reads) | | |
|---|---|---|---|---|---|---|---|
| ID | Round 5 Multi-plicity | Round 3 Rank | Round 3 Multi-plicity | ID | Round 5 Multi-plicity | Round 3 Rank | Round 3 Multi-plicity |
| hHSF1-R5-13 | 170782 | 5 | 190 | hHSF2-R5-13 | 176490 | 162 | 50 |
| hHSF1-R5-14 | 156627 | 41 | 66 | hHSF2-R5-14 | 146975 | 41 | 98 |
| hHSF1-R5-15 | 143621 | 26 | 89 | hHSF2-R5-15 | 139564 | 650 | 22 |
| hHSF1-R5-16 | 127020 | 2 | 347 | hHSF2-R5-16 | 123854 | 45 | 97 |
| hHSF1-R5-17 | 98130 | 40 | 68 | hHSF2-R5-17 | 121634 | 108 | 61 |
| hHSF1-R5-18 | 97392 | 8 | 154 | hHSF2-R5-18 | 117221 | 10 | 189 |
| hHSF1-R5-19 | 84796 | 35 | 73 | hHSF2-R5-19 | 87884 | 1 | 242 |
| hHSF1-R5-20 | 76493 | 43 | 64 | hHSF2-R5-20 | 86977 | 11 | 161 |

The top twenty highest multiplicity candidate aptamers from Round 5 pools for hHSF1 and hHSF2 (total number of sequencing reads = 5,930,382 and 8,644,268 respectively) and the corresponding Round 3 ranks and multiplicities (total number of sequencing reads = 8,072,400 and 9,350,602 respectively). To compare multiplicity values from different pools, the results are presented as multiplicity per 10 million reads.

Figure 17A:
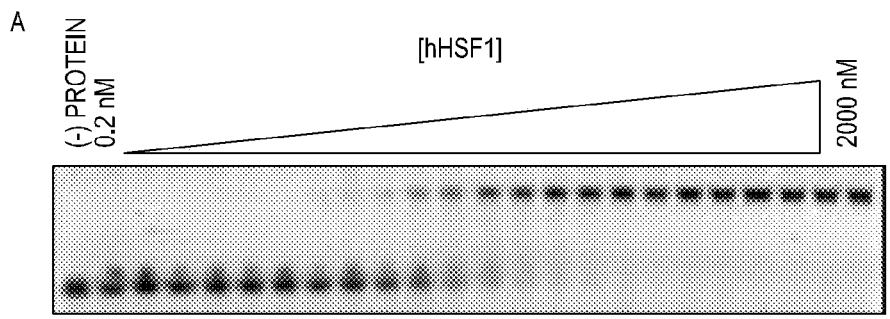
FIGS. 17A-17C. Evaluation of candidate aptamers binding to target proteins. Typical F-EMSA results for hHSF1-R5-1 aptamer binding to a two-thirds dilution series (from 2000 nM to 0.2 nM) of hHSF1 protein (FIG. 17A). Panels B (FIG. 17B) and C (FIG. 17C) are the binding curves measured by F-EMSA for the hHSF1-R5-1 and hHSF2-R5-2 aptamers to hHSF1, hHSF2, dHSF and GST-tag. The same dilution series in FIG. 17A was used in FIG. 17B and FIG. 17C. The solid lines are the best-fits of the Hill equation to the experimental data for each aptamer-target pair with the appropriate $K_D$ values given in the figure legends.
Figure 17B:
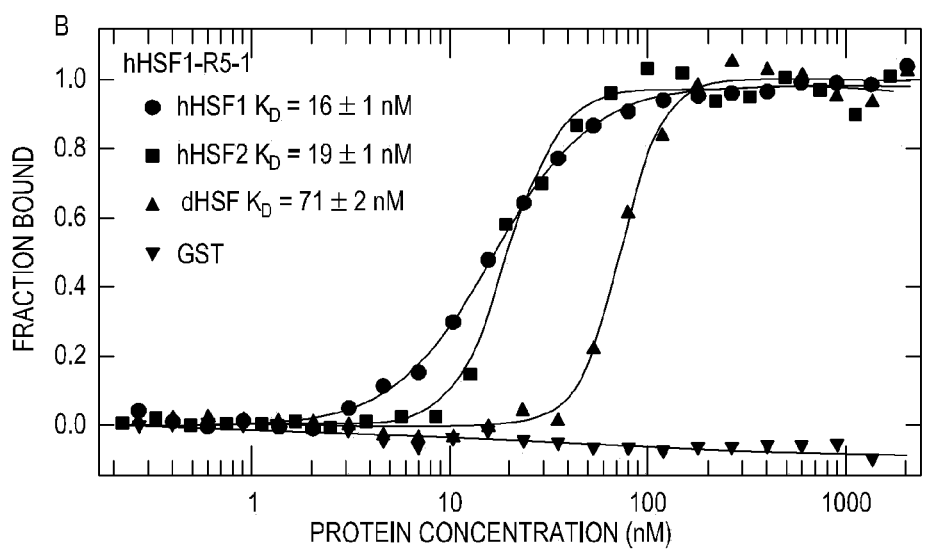
Figure 17C:
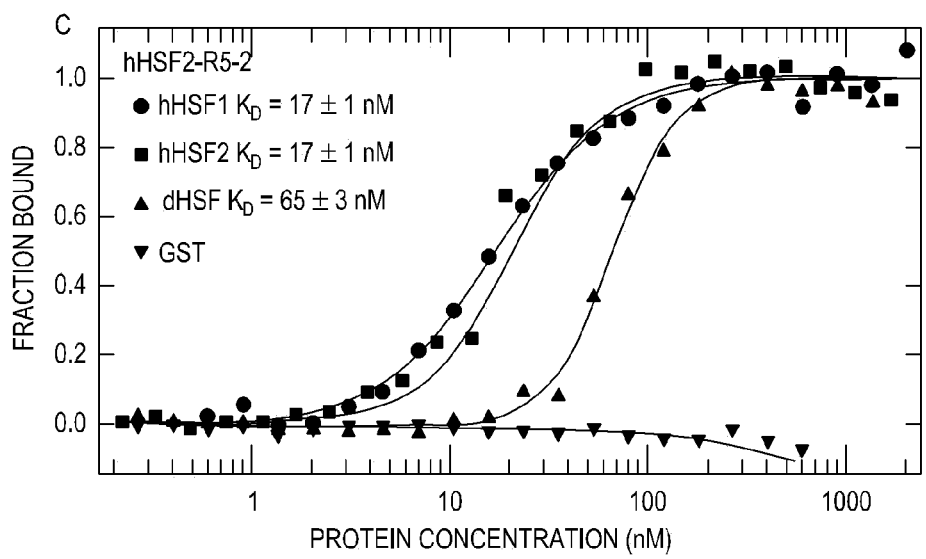

The putative RNA aptamers were fluorescently end-labeled and then tested for binding to their hHSF targets using F-EMSA and FP assays (Ref. 16). An image of a typical F-EMSA result is shown in FIG. 17A for hHSF1-R5-1 aptamer binding to hHSF1 protein. The fraction of bound aptamer was calculated as a function of protein concentration and then plotted as shown in FIGS. 17B and 17C for various aptamer-protein pairings; $K_D$ values were determined by fitting each data set to the Hill equation. Overall, both aptamers showed high affinity binding to hHSF1 and hHSF2 ($K_D$<20 nM). Interestingly, both aptamers also bound to hexahistidine-tagged dHSF, although slightly weaker ($K_D$~70 nM), and no binding was observed to the GST-tag alone. The F-EMSA results were confirmed by the FP assays (FIGS. 22 and 23). Thus, the observed binding is not due to the affinity tags on the protein targets but rather specific domains of the targets themselves. Given that the highest degree of sequence similarity between hHSF1, hHSF2, and dHSF is in the DNA binding and trimerization domains (DBD-TD) (Ref. 26) and the previously selected dHSF aptamer was found to bind the DBD-TD of dHSF (Ref. 21), we predict these novel hHSF aptamers are likely to bind the HSF proteins in a similar fashion. Contrary to their functional similarity, these two aptamers did not show any similarity in secondary structure as predicted by mFold (Ref. 27) (FIG. 21). Although beyond the scope of the present work, the detailed mechanism of these and other potential aptamers' binding to HSF proteins as well as the consequences of binding await further study. However, successful selection of two distinct high-affinity aptamers, hHSF1-R5-1 and hHSF2-R5-2, targeting two closely related proteins, hHSF1 and hHSF2, respectively, in a single selection demonstrates that our microcolumn-based SELEX technology is capable of yielding high-affinity aptamers ($K_D$<20 nM) in as little as five rounds of selection whereas most conventional SELEX methods require typically twelve rounds of selection (Ref. 7).

Conclusions

We have developed a microcolumn-based technology for the efficient selection of nucleic acid aptamers for multiple targets. Our microcolumns have a number of advantages over other chromatography based processes. First, they can be readily assembled in various configurations to accommodate multiple targets during the selection step—as a proof of principle we used a single aliquot of starting RNA aptamer library to perform selections to four different immobilized target proteins in separate microcolumns. Second, either as assembled or disassembled units, they do not require any specialized equipment to perform the selection step—we used a multi-rack syringe pump to control the solution flow rates during the selection step. Third, they require very little amounts of resin and target molecules. For this study, we focused on the selection of RNA aptamers; however, our approach would also work for DNA aptamers. The multiplex selection presented in this work is simpler and thus easier to perform than previous microfluidic techniques using sol-gel chemistry (Ref. 8). Also, compared to filter plate based methods (Ref. 9), our modular columns allow 'counter-selections' to be done simultaneously with the selection step to enhance target specificity.

The overall performance of our devices was evaluated in two different sets of experiments. In the first, we looked at a single selection step and optimized its performance by monitoring the enrichment of GFPapt, a known RNA aptamer for GFP. The performance was strongly dependent on the amount of target immobilized onto the resin and the flow rates for both the loading and washing steps. In the second, we used the optimal conditions as part of a selection and amplification strategy to verify specific GFPapt partitioning over three protein preparations (UBLCP1, CHK2, and GFP) followed by a complete multiplex selection against hHSF1 and hHSF2. High-throughput sequencing analysis of the selected pools from multiple rounds showed an enrichment of specific aptamer sequences. For hHSF1 and hHSF2, the sequences from Round 5 with the highest multiplicity values also had high inter-round enrichments. Those sequences were target specific and could be easily identified as being preferentially enriched after just three selection rounds. We tested a single candidate each to hHSF1 and hHSF2 and found both to be high affinity aptamers to full length hHSFs.

Although HSF proteins have been extensively studied and characterized, we are still limited by the available methods and lack approaches to perturb the activity of specific factors to tease apart molecular interactions. Aptamers can act as inhibitors that bind to a protein surface and disrupt specific interactions or functions. When expressed in vivo in a temporally and spatially controlled manner, these aptamers provide a way to rapidly disrupt targeted domains of proteins and efficiently assess their primary functions and mechanisms of actions. We previously demonstrated the utility of inhibitory RNA aptamers to study macromolecular interactions in vivo (Refs. 21, 22, and 28). However, there were some limitations on the methodology used to select those aptamers, and we believe that our new method will significantly improve the SELEX efficiency: 1) allowing the selection of aptamers for many targets including different domains of a single protein at the same time, and 2) reducing the number of SELEX rounds to achieve the selection of high-affinity aptamers. With this multiplexed technology, we believe it will be possible to efficiently select aptamers that bind to the distinct domains of HSF and other proteins, which will be extremely valuable to study the interactions of these proteins.

Extensions of the microcolumn devices and approach developed in this work could be used for selection strategies with various combinatorial libraries including but not limited to genomic sequences (Ref. 29), mRNA display (Ref. 30), and peptide nucleic acids (Ref. 31). Also, our multiplex approach would easily facilitate the discovery of multivalent aptamers to distinct target binding sites (Ref. 32) by performing a final selection using serially arranged microcolumns with different target subunits in each. Finally, our microcolumn devices could be used to discriminate for aptamers based on their on-rate or off-rate binding characteristics by enforcing certain restrictions on the flow rates used for the loading step and washing step respectively (Ref. 33).

Example 3

Additional Information: Multiplexed Microcolumn-Based Process for Efficient Selection of RNA Aptamers This example provides supporting information relating to the embodiment of a reusable microcolumn and process for the efficient discovery of nucleic acid aptamers for multiple target molecules set forth in Example 2.

Materials and Methods

Selection Simulations

Simulation conditions were set to mimic experimental conditions wherever possible including: (i) concentration of target, (ii) microfluidic dimensions, (iii) flow-rate during library loading, (iv) volume and concentration of the library, and (v) flow-rate and duration of washing. A discrete distribution of KD within the starting library was assumed to be log-normal (Berg, O. G. and von Hippel, P. H. *J Mol Biol* 1987, 193(4), 723-743) with only 0.00011% of the aptamers being the strongest binders. However our simulation results proved to be very insensitive to these initial conditions due to the significantly greater concentration of target than aptamers. The on-rate ($k_a$) and off-rate (kd) constants for each aptamer were approximated to match select experimental conditions: kd*ka=0.04. Further, the simulations included the presence of a background binding possibility for all aptamers. Regardless of the binding strength of the aptamers to the target, each aptamer was capable of binding to a non-specific binding site with an equilibrium binding constant of 10 µM with a non-specific binding site concentration of 100 µM; these parameters were determined to sufficiently match the background binding experimentally observed.

Preparation of Recombinant Protein Targets

Recombinant proteins were expressed in BL21(DE3)-RIPL *E. coli* cells (Agilent Technologies) transformed with plasmids that encode for hexahistidine-tagged GFP, CHK2, UBLCP1, and dHSF, or GST-tagged hHSF1 and hHSF2 (Table 2). Two or four liter LB cultures supplemented with 100 jtg/ml ampicillin were inoculated with starter LB culture derived from a single colony and grown at 37° C. until the $OD_{600}$ reached approximately 0.6. Protein expression was induced by the addition of IPTG to a final concentration of 1 mM. After an additional incubation, bacteria were collected by centrifugation and the resulting pellet was processed according to the manufacturer's instructions for Ni-NTA Superflow (Qiagen) or Glutathione-agarose (Thermo Scientific) resins. SDS-polyacrylamide gel electrophoresis (SDS-PAGE) was used to verify the purity and quality of the final protein product. Resulting protein preps were dialyzed against 1×PBS (supplemented with 5 mM 2-mercaptoethanol and 0.01% Triton X100) and stored in small aliquots after addition of glycerol to a final concentration of 20%.

Preparation of Nucleic Acid Library and GFP-Binding Aptamer

The 120-nt DNA library consists of a 70-nt random region flanked by two constant regions: 5'-AAGCTTCGTCAAGTCTGCAGTGAA-N70-GAATTCGTAGATGTG-GATCCATTCCC-3' (SEQ ID NO:23). The single-stranded DNA template library was converted to double-stranded DNA while introducing the T7 promoter using Klenow exo-(NEB) and Lib-FOR oligo: 5'-GATAATACGACTCAC-TATAGGGAATGGATCCACATCTACGA-3' (SEQ ID NO:24). The resulting library was later amplified in a 1 L PCR reaction using Taq DNA polymerase, Lib-FOR oligo, and Lib-REV oligo: 5'-AAGCTTCGTCAAGTCTGCAG TGAA-3' (SEQ ID NO:25). A single aliquot covering the complexity of the entire library was transcribed with T7 RNA polymerase in a 88 mL reaction yielding 1200-fold amplification. An aliquot of this RNA library corresponds to an average of 4 to 6 copies of each sequence in the $5 \times 10^{15}$ library was used as the starting pool for selections.

GFPapt, the 84-nt GFP binding RNA aptamer, has the following sequence: 5'-AGCUUCUGGACUGC-GAUGGGAGCACGAAACGUCGUGGCG-CAAUUGGGUGGGG AAAGUCC UUAAAAGAGGGC-CACCACAGAAGCU-3' (SEQ ID NO:26). The forward and reverse oligos used for qPCR analyses were GFPapt-FOR: 5'-GCTTCTGGACTGCG ATGGGAGCA-3' (SEQ ID NO:27) and GFPapt-REV: 5'-GCTTCTGTGGTGGCC CTCTTTTAAGGACT-3' (SEQ ID NO:28).

All of the oligos used in this work were obtained from Integrated DNA Technologies.

High-Throughput Sequencing, Data Filtering, and Clustering Analyses

The barcoded adapter-ligated PCR products were PAGE-purified, phenol:chloroform and chloroform extracted, ethanol precipitated, and then re-suspended in 10 mM Tris-HCl pH 7.5 buffer. High-throughput sequencing (100 nt single-end reads) was performed by the sequencing core facility at Life Sciences Core Laboratories Center, Cornell University. Up to twelve barcoded samples were successfully sequenced in a single lane of the HiSeq 2000 flow-cell.

Sequences that contained any ambiguity or had a quality score less than three (Illumina 1.8 encoding) were removed from analysis. Remaining sequences were separated based on the barcodes using the 'FASTX' toolkit (hannonlab.cshl.edu/fastx_toolkit) by requiring a perfect match for barcode sequences. The forward constant regions were stripped via semi-global alignment using 'cutadapt' (Martin, M. *EMBnet.journal* 2011, 17(1), 10-12); given the length of the reads, the reverse constant region and Illumina sequencing adaptors were not present and did not need to be removed. Remaining sequences containing between 64 and 72 nucleotides of the random region (inclusively) and identical in sequence were collapsed using the FASTX tool kit. A two-stage clustering approach was applied to the collapsed sequences to account for sequencing error that may induce apparently distinct reads from a single aptamer. Sequences with multiplicity at most one in all pools (i.e., singletons) that are dissimilar from all other non-singleton sequences in their respective pools, as determined by using 'USEARCH' (Edgar, R. C. *Bioinformatics* 2010, 26(19), 2460-2461) to align each to a database of non-singleton reads, are likely to be spurious or present at relatively low levels. For improved computational efficiency these were excluded from subsequent analysis. Remaining sequences were aggregated across pools and those with 80% sequence identity were clustered using USEARCH. The highest multiplicity read within each cluster, the cluster representative, was identified as the true aptamer sequence. The multiplicity of this cluster was defined as the sum of multiplicities within the cluster. Representative sequences, multiplicities and enrichment factors (defined as the ratio of the fraction of a given cluster in a given pool/fraction of the same cluster in the starting library) for each cluster were tabulated and sorted based on the multiplicity or the enrichment factor across different pools to select candidate aptamers for each target.

Amplification of Select Aptamer Sequences From Pools

Candidate aptamer sequences were PCR amplified from the final Round 5 pool for each target using an aptamer specific oligo and the Lib-REV oligo with Phusion Polymerase (NEB), according to manufacturer's instructions. Aptamer specific oligos span the forward constant region and ~30 nt of the random region ($T_m$ of 60° C.) of each aptamer. The resulting PCR product was double-digested with EcoRI or BamHI, and PstI or HindIII, and ligated into a similarly cut pGEM3Z-N70Apt plasmid, which has been obtained by cloning a random aptamer sequence together with the T7 promoter into the pGEM3Z vector (Promega) between NarI and HindIII sites. Multiple clones, typically 3 to 10, were sequenced to obtain a consensus for the full-length sequence of the candidate aptamer. Note, high-throughput sequencing only yielded the first 68 nt sequence of the 70 nt random region (100 nt sequencing–26 nt forward constant region–6 nt barcode). Therefore, all of the candidate aptamers that were used in subsequent assays were prepared from the sequence verified constructs to ensure the purity of the intended aptamer in each preparation.

Fluorescence Polarization (FP) Assay

Binding reactions were prepared by mixing 2 nM of 3'-end labeled RNA aptamer with protein concentrations that varied from 0.2 to 2000 nM in 1.5-fold increments in binding buffer containing 0.01% IGEPAL CA630, 10 µg/ml tRNA, and 3 U of SUPERase•In RNase Inhibitor (Invitrogen). The reactions were prepared in black 96-well half area microplates (Corning) and then incubated at room temperature for 2 hours. The plates were read on a Synergy H1 Microplate Reader (BioTek); fluorescence polarization was measured as $(F_\| - F^\perp)/(F_\| + F^\perp)$ using the Ex: 485/20 Em: 528/20 filter set.

REFERENCES

Citation of a reference herein shall not be construed as an admission that such reference is prior art to the present invention. All references cited herein are hereby incorporated by reference in their entirety. Below is a listing of various references cited herein by Reference ("Ref.") number:

1. Ciesiolka, J.; et al. M. *RNA* 1995, 1, 538-550.
2. Shangguan, D.; et al. *Proc Natl Acad Sci USA* 2006, 103(32), 11838-11843.
3. Tombelli, S. and Mascini, M. *Curr Opin Mol Ther* 2009, 11(2), 179-188.
4. Joyce, G. F. *Gene* 1989, 82(1), 83-87.
5. Ellington, A. D. and Szostak, J. W. *Nature* 1990, 346, 818-822.
6. Tuerk, C. and Gold, L. *Science* 1990, 249(4968), 505-510.
7. Gopinath, S. C. B. *Anal Bioanal Chem* 2007, 387(1), 171-182.
8. Park, S.; et al. *Lab Chip* 2009, 9(9), 1206-1212.
9. Jolma, A.; et al. *J. Genome Res* 2010, 20(6), 861-873.
10. Nieuwlandt, D.; et al. *Biochemistry* 1995, 34, 5651-5659.
11. Liu, J. and Stormo, G. D. *Nucleic Acids Res* 2005, 33(17), e141.
12. Cheng, C.; et al. *Biochem Biophys Res Commun* 2008, 366(3), 670-674.
13. Holeman, L. A.; et al. *Fold Des* 1998, 3(6), 423-231.
14. Shui B, et al. *Nucleic Acids Res* 2012, 40(5), e39.
15. Cox, J. C.; et al. *Biotechnol Prog* 1998, 14(6), 845-850.
16. Pagano, J. M.; et al. *J Biol Chem* 2007, 282(12), 8883-8894.
17. Eulberg, D.; et al. *Nucleic Acids Res* 2005, 33(4), e45.
18. Nitsche, A.; et al. *BMC Biotechnol* 2007, 7, 48.
19. Leventis, R. and Silvius, J. R. *Biophys J* 2010, 99(7), 2125-2133.
20. Dai, C.; et al. *Cell* 2007, 130(6), 1005-1018.
21. Zhao, X.; et al. *Nucleic Acids Res* 2006, 34(13), 3755-3761.
22. Salamanca, H. H.; et al. *Nucleic Acids Res* 2011, 39(15), 6729-6740
23. Unpublished work, Cornell University, 2009
24. Zimmermann, B.; et al. *PLoS One* 2010, 5(2), e9169.
25. Cho, M.; et al. *Proc Natl Acad Sci USA* 2010, 107(35), 15373-15378.
26. Anckar, J. and Sistonen, L. *Adv Exp Med Biol* 2007, 594, 78-88.
27. Zuker, M. *Nucleic Acids Res* 2003, 31(13), 3406-3415.
28. Shi, H.; et al. *Proc Natl Acad Sci USA* 1999, 96(18), 10033-10038.
29. Singer, B. S.; et al. *Nucleic Acids Res* 1997, 25(4), 781-786.
30. Wilson, D. S.; et al. *Proc Natl Acad Sci USA* 2001, 98(7), 3750-3755.
31. Brudno, Y.; et al. *Nat Chem Biol* 2010, 6, 148-155.
32. Gong, Q.; et al. *Anal Chem* 2012, 84(12), 5365-5371.
33. Gold, L.; et al. *PLoS ONE* 2010, 5(12), e15004.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed is:

1. A microcolumn device for selecting nucleic acid aptamers for single and multiple target molecules, said microcolumn device comprising:
 a body comprising an inlet end and a directly opposing outlet end, a recessed portion extending into the body from the outlet end and forming a compartment for housing a frit, and a microfluidic channel disposed between the inlet end and the recessed portion, wherein the microfluidic channel has a volume capacity of between about 0.5 µL and about 250 µL;
 a frit disposed in the recessed portion; and
 a pair of adapters comprising an inlet adapter bonded to the inlet end of the body and a directly opposing outlet adapter bonded to the outlet end of the body, wherein each adapter includes a hollow passageway for passing a liquid sample there through, and wherein each adapter includes a connector region for effectuating serial fluid communication of a plurality of microcolumn devices.

2. The microcolumn device according to claim 1, wherein the body comprises a biocompatible plastic polymer selected from the group consisting of poly(ethylene terephthalate glycol) (PETg), polyvinyl chloride (PVC), and poly(methyl methacrylate) (PMMA).

3. The microcolumn device according to claim 1 further comprising:
 an affinity chromatography resin disposed in the microfluidic channel of the body.

4. The microcolumn device according to claim 3, wherein the affinity chromatography resin comprises an immobilized target molecule.

5. The microcolumn device according to claim 4, wherein the immobilized target is labeled.

6. The microcolumn device according to claim 4, wherein the immobilized target molecule is a protein or polypeptide, a carbohydrate, a lipid, a small molecule, a pharmaceutical agent, an organic non-pharmaceutical agent, a macromolecular complex, a virus particle, or a cell.

7. The microcolumn device according to claim 4, wherein the immobilized target molecule is provided from a mixture of lysed cells, or a mixture of purified, partially purified, or non-purified protein.

8. A system for selecting nucleic acid aptamers for single and multiple target molecules, said system comprising:
 a plurality of microcolumn devices in serial fluid communication with one another, wherein each microcolumn device comprises:
 a body comprising an inlet end and a directly opposing outlet end, a recessed portion extending into the body from the outlet end and forming a compartment for housing a frit, and a microfluidic channel disposed between the inlet end and the recessed portion, wherein the microfluidic channel has a volume capacity of between about 0.5 µL and about 250 µL;
 a frit disposed in the recessed portion; and
 a pair of adapters comprising an inlet adapter bonded to the inlet end of the body and a directly opposing outlet adapter bonded to the outlet end of the body, wherein each adapter includes a hollow passageway for passing a liquid sample there through, and wherein each adapter includes a connector region for effectuating serial fluid communication of the plurality of microcolumn devices.

9. The system according to claim 8 further comprising:
 an affinity chromatography resin disposed in the microfluidic channel of the body of each microcolumn device.

10. The system according to claim 9, wherein the affinity chromatography resins contained in each microcolumn device are the same or different.

11. The system according to claim 9, wherein the affinity chromatography resin comprises an immobilized target molecule, said immobilized target molecule being labeled or unlabeled.

12. The system according to claim 11, wherein the immobilized target molecules contained in each microcolumn device are the same or different.

13. The system according to claim 8, wherein union connectors are used to effectuate the serial fluid communication of the plurality of microfluidic devices.

14. A method of making a microcolumn device for selecting nucleic acid aptamers for single and multiple target molecules, said method comprising:
 providing a body comprising an inlet end and a directly opposing outlet end, a recessed portion extending into the body from the outlet end and forming a compartment for housing a frit, and a microfluidic channel disposed between the inlet end and the recessed portion, wherein the microfluidic channel has a volume capacity of between about 0.5 µL and about 250 µL;
 disposing a fit in the recessed portion of the body; and
 attaching a pair of adapters to the body, wherein an inlet adapter is bonded to the inlet end of the body and a directly opposing outlet adapter is bonded to the outlet end of the body, wherein each adapter includes a hollow passageway for passing a liquid sample there through, and wherein each adapter includes a connector region for effectuating serial fluid communication of multiple microcolumn devices.

15. The method according to claim 14, wherein the body comprises a biocompatible plastic polymer selected from the group consisting of poly(ethylene terephthalate glycol) (PETg), polyvinyl chloride (PVC), and poly(methyl methacrylate) (PMMA).

16. The method according to claim 14 further comprising:
 disposing an affinity chromatography resin in the microfluidic channel of the body.

17. The method according to claim 16, wherein the affinity chromatography resin comprises an immobilized target molecule.

18. The method according to claim 17, wherein the immobilized target is labeled.

19. The method according to claim 17, wherein the immobilized target molecule is a protein or polypeptide, a carbohydrate, a lipid, a small molecule, a pharmaceutical agent, an organic non-pharmaceutical agent, a macromolecular complex, a virus particle, or a cell.

20. The method according to claim 17, wherein the immobilized target molecule is provided from a mixture of lysed cells, or a mixture of purified, partially purified, or non-purified protein.

21. A kit comprising one or more microcolumn devices according to claim 1.

22. The kit according to claim 21 further comprising one or more of the following:
 one or more affinity chromatography resins, one or more labels for tagging a target molecule of interest, a random pool of nucleic acid molecules, wash buffer, binding buffer, blocking buffer, reagents for carrying out reverse transcription, polymerase chain reaction, and/or transcription, and directions for carrying out selection of aptamers to multiple target molecules using a plurality of the microcolumn devices connected in series and subsequently arranged in a standalone or parallel configuration.

23. A kit comprising a system according to claim 8.

24. The kit according to claim 23 further comprising one or more of the following:
one or more affinity chromatography resins, one or more labels for tagging a target molecule of interest, a random pool of nucleic acid molecules, wash buffer, binding buffer, blocking buffer, reagents for carrying out reverse transcription, polymerase chain reaction, and/or transcription, and directions for carrying out selection of aptamers to multiple target molecules using a plurality of the microcolumn devices connected in series and subsequently arranged in a standalone or parallel configuration.

25. The microcolumn device according to claim 1, wherein said frit is effective to maintain an affinity chromatography resin in the microfluidic channel while at the same time allow a liquid sample to pass through the frit and then out of the outlet end of the body.

26. The microcolumn device according to claim 1, wherein said frit is made of a material selected from the group consisting of a porous polymer and stainless steel.

27. The system according to claim 8, wherein said frit is effective to maintain an affinity chromatography resin in the microfluidic channel while at the same time allow a liquid sample to pass through the frit and then out of the outlet end of the body.

28. The system according to claim 8, wherein said frit is made of a material selected from the group consisting of a porous polymer and stainless steel.

29. The method according to claim 14, wherein said frit is effective to maintain an affinity chromatography resin in the microfluidic channel while at the same time allow a liquid sample to pass through the frit and then out of the outlet end of the body.

30. The method according to claim 14, wherein said frit is made of a material selected from the group consisting of a porous polymer and stainless steel.

* * * * *

SEQUENCE LISTING

<160> NUMBER OF SEQ ID NOS: 28

<210> SEQ ID NO 1
<211> LENGTH: 72
<212> TYPE: DNA
<213> ORGANISM: Artificial
<220> FEATURE:
<223> OTHER INFORMATION: cDNA of reverse transcribed RNA aptamers

<400> SEQUENCE: 1
attcgatcgg ttccaacgct ctgtcgccta agtgaacaga tgaagaaaaa atagcccaat    60
aagaggcaac aa                                                      72

<210> SEQ ID NO 2
<211> LENGTH: 72
<212> TYPE: DNA
<213> ORGANISM: Artificial Sequence
<220> FEATURE:
<223> OTHER INFORMATION: cDNA of reverse transcribed RNA aptamers

<400> SEQUENCE: 2
attccaagcc ttcactccgc aaaatacgcg cttccaaata ataacaataa gaacacctag    60
gaagcaacgc gc                                                      72

<210> SEQ ID NO 3
<211> LENGTH: 72
<212> TYPE: DNA
<213> ORGANISM: Artificial Sequence
<220> FEATURE:
<223> OTHER INFORMATION: cDNA of reverse transcribed RNA aptamers

<400> SEQUENCE: 3
attccaacga gatacaataa taacaataac caccccgatt cgttccgtga tccataaatc    60
gagcatgcac ac                                                      72

<210> SEQ ID NO 4
<211> LENGTH: 72
<212> TYPE: DNA
<213> ORGANISM: Artificial Sequence
<220> FEATURE:
<223> OTHER INFORMATION: cDNA of reverse transcribed RNA aptamers

<400> SEQUENCE: 4
attcacaagc tttatcctaa cagccagaga cctcaccacc cagagaagag cagagttgca    60
taagcaacca tg                                                      72

<210> SEQ ID NO 5
<211> LENGTH: 72
<212> TYPE: DNA
<213> ORGANISM: Artificial Sequence
<220> FEATURE:
<223> OTHER INFORMATION: cDNA of reverse transcribed RNA aptamers

<400> SEQUENCE: 5
attcatacac ttcatcaccc cagagctgtg ttgctgaaag gcctacctac agagaagaac    60
aagagccacc ag                                                      72

<210> SEQ ID NO 6
<211> LENGTH: 72
<212> TYPE: DNA
<213> ORGANISM: Artificial Sequence
<220> FEATURE:
<223> OTHER INFORMATION: cDNA of reverse transcribed RNA aptamers

```
<400> SEQUENCE: 6
attccagtcc tagcacaaga ctgcaacgtg gatatgaccc catactgact aacaataaca    60
acaaggtagg ga                                                        72

<210> SEQ ID NO 7
<211> LENGTH: 72
<212> TYPE: DNA
<213> ORGANISM: Artificial Sequence
<220> FEATURE:
<223> OTHER INFORMATION: cDNA of reverse transcribed RNA aptamers

<400> SEQUENCE: 7
attccataca ttgcccacgg ctccgagcga taacctgcaa acgctcacta tctaacaaaa    60
gcaaaaacct gt                                                        72

<210> SEQ ID NO 8
<211> LENGTH: 72
<212> TYPE: DNA
<213> ORGANISM: Artificial Sequence
<220> FEATURE:
<223> OTHER INFORMATION: cDNA of reverse transcribed RNA aptamers

<400> SEQUENCE: 8
attactaccg tcccacaata ataataacaa caaagggcga gattatttcg taacactgga    60
ccgacgagtt ta                                                        72

<210> SEQ ID NO 9
<211> LENGTH: 72
<212> TYPE: DNA
<213> ORGANISM: Artificial Sequence
<220> FEATURE:
<223> OTHER INFORMATION: cDNA of reverse transcribed RNA aptamers

<400> SEQUENCE: 9
attctttccg cccttcgcgt acttaagccc ataccagtga tccgtataaa aataataata    60
ataaccatcg ga                                                        72

<210> SEQ ID NO 10
<211> LENGTH: 72
<212> TYPE: DNA
<213> ORGANISM: Artificial Sequence
<220> FEATURE:
<223> OTHER INFORMATION: cDNA of reverse transcribed RNA aptamers

<400> SEQUENCE: 10
attctcacct acaacgctta cccaatcttc gcccagttgc gaatggctga agacccgata    60
agaggttgag cc                                                        72

<210> SEQ ID NO 11
<211> LENGTH: 72
<212> TYPE: DNA
<213> ORGANISM: Artificial Sequence
<220> FEATURE:
<223> OTHER INFORMATION: cDNA of reverse transcribed RNA aptamers

<400> SEQUENCE: 11
attcatccta atatcctaaa gtcgatcact gagccagcct ggaccgataa caacaacaac    60
aaagcgacta ct                                                        72

<210> SEQ ID NO 12
```

<211> LENGTH: 72
<212> TYPE: DNA
<213> ORGANISM: Artificial Sequence
<220> FEATURE:
<223> OTHER INFORMATION: cDNA of reverse transcribed RNA aptamers

<400> SEQUENCE: 12
attccaaagg ccacctagaa gccaaaccaa agagaatcta caggacccat actcagcata    60
cagagagcac tg    72

<210> SEQ ID NO 13
<211> LENGTH: 72
<212> TYPE: DNA
<213> ORGANISM: Artificial Sequence
<220> FEATURE:
<223> OTHER INFORMATION: cDNA of reverse transcribed RNA aptamers

<400> SEQUENCE: 13
attcatgacc agttcacctt aggtctacgg ctaggaatct aggattaaat aataataaca    60
acaaattcca tc    72

<210> SEQ ID NO 14
<211> LENGTH: 72
<212> TYPE: DNA
<213> ORGANISM: Artificial Sequence
<220> FEATURE:
<223> OTHER INFORMATION: cDNA of reverse transcribed RNA aptamers

<400> SEQUENCE: 14
attctcccaa caggagactt cgcaccctcc atctccgaaa actgcaaaca ggacatacaa    60
caacaataat aa    72

<210> SEQ ID NO 15
<211> LENGTH: 72
<212> TYPE: DNA
<213> ORGANISM: Artificial Sequence
<220> FEATURE:
<223> OTHER INFORMATION: cDNA of reverse transcribed RNA aptamers

<400> SEQUENCE: 15
attccgagcc aaagtcataa ccaaccagtg ataatccaac agagcccaaa cgccagccat    60
taagagcaaa cg    72

<210> SEQ ID NO 16
<211> LENGTH: 72
<212> TYPE: DNA
<213> ORGANISM: Artificial Sequence
<220> FEATURE:
<223> OTHER INFORMATION: cDNA of reverse transcribed RNA aptamers

<400> SEQUENCE: 16
attcccggct tgttacaaa atagcgaaac gataagaggg gaaaaccccc gccgccgcaa    60
taagacgacg ta    72

<210> SEQ ID NO 17
<211> LENGTH: 72
<212> TYPE: DNA
<213> ORGANISM: Artificial Sequence
<220> FEATURE:
<223> OTHER INFORMATION: cDNA of reverse transcribed RNA aptamers

<400> SEQUENCE: 17
attcataaac tcctgtcaac agttctgcaa tgcatacgca ttacgccata ataacaataa    60

```
taagaagcgc gc                                                        72

<210> SEQ ID NO 18
<211> LENGTH: 72
<212> TYPE: DNA
<213> ORGANISM: Artificial Sequence
<220> FEATURE:
<223> OTHER INFORMATION: cDNA of reverse transcribed RNA aptamers

<400> SEQUENCE: 18
attcattcgc acgataccta cgtaaacttt ccgaagcagg aactatttag aagcagaaaa    60
aaccagccac tt                                                        72

<210> SEQ ID NO 19
<211> LENGTH: 72
<212> TYPE: DNA
<213> ORGANISM: Artificial Sequence
<220> FEATURE:
<223> OTHER INFORMATION: cDNA of reverse transcribed RNA aptamers

<400> SEQUENCE: 19
atccacacaa caccaataat aacccatctg aaatagtccc aatgtaaaag ccaagtgcga    60
aaacaaatta gg                                                        72

<210> SEQ ID NO 20
<211> LENGTH: 72
<212> TYPE: DNA
<213> ORGANISM: Artificial Sequence
<220> FEATURE:
<223> OTHER INFORMATION: cDNA of reverse transcribed RNA aptamers

<400> SEQUENCE: 20
attcagcatc gcccacggcg ctccaggtcg tatgacagca tgtccaatac aaaaccaata    60
acaacgagga ca                                                        72

<210> SEQ ID NO 21
<211> LENGTH: 117
<212> TYPE: RNA
<213> ORGANISM: Artificial Sequence
<220> FEATURE:
<223> OTHER INFORMATION: RNA aptamer

<400> SEQUENCE: 21
gggaauggau ccacaucuac gaauucaauc aaguccccag acucagcaac acuggacagc    60
gauaugcaga uaaccaagac caauucacuc caguucacug cagacuugac gaagcuu     117

<210> SEQ ID NO 22
<211> LENGTH: 117
<212> TYPE: RNA
<213> ORGANISM: Artificial Sequence
<220> FEATURE:
<223> OTHER INFORMATION: RNA aptamer

<400> SEQUENCE: 22
gggaauggau ccacaucuac gaauucaauc aaguccccag acucagcaac acuggacagc    60
gauaugcaga uaaccaagac caauucacuc caguucacug cagacuugac gaagcuu     117

<210> SEQ ID NO 23
<211> LENGTH: 120
<212> TYPE: DNA
<213> ORGANISM: Artificial Sequence
<220> FEATURE:
```

<223> OTHER INFORMATION: Artificial DNA library sequence
<220> FEATURE:
<221> NAME/KEY: misc_feature
<222> LOCATION: (25)..(94)
<223> OTHER INFORMATION: 70-nt random region

<400> SEQUENCE: 23
aagcttcgtc aagtctgcag tgaannnnnn nnnnnnnnnn nnnnnnnnnn nnnnnnnnnn    60
nnnnnnnnnn nnnnnnnnnn nnnnnnnnnn nnnngaattc gtagatgtgg atccattccc   120

<210> SEQ ID NO 24
<211> LENGTH: 41
<212> TYPE: DNA
<213> ORGANISM: Artificial Sequence
<220> FEATURE:
<223> OTHER INFORMATION: Promoter

<400> SEQUENCE: 24
gataatacga ctcactatag ggaatggatc cacatctacg a                        41

<210> SEQ ID NO 25
<211> LENGTH: 24
<212> TYPE: DNA
<213> ORGANISM: Thermus aquaticus

<400> SEQUENCE: 25
aagcttcgtc aagtctgcag tgaa                                           24

<210> SEQ ID NO 26
<211> LENGTH: 84
<212> TYPE: RNA
<213> ORGANISM: Artificial Sequence
<220> FEATURE:
<223> OTHER INFORMATION: RNA aptamer

<400> SEQUENCE: 26
agcuucugga cugcgauggg agcacgaaac gucguggcgc aauugggugg ggaaaguccu    60
uaaaagaggg ccaccacaga agcu                                           84

<210> SEQ ID NO 27
<211> LENGTH: 23
<212> TYPE: DNA
<213> ORGANISM: Artificial Sequence
<220> FEATURE:
<223> OTHER INFORMATION: Primer

<400> SEQUENCE: 27
gcttctggac tgcgatggga gca                                            23

<210> SEQ ID NO 28
<211> LENGTH: 29
<212> TYPE: DNA
<213> ORGANISM: Artificial Sequence
<220> FEATURE:
<223> OTHER INFORMATION: Primer

<400> SEQUENCE: 28
gcttctgtgg tggccctctt ttaaggact                                      29